United States Patent [19]

Engel et al.

[11] Patent Number: 6,156,702
[45] Date of Patent: Dec. 5, 2000

[54] SUBSTITUTED 4-BENZOYLPYRAZOLES

[75] Inventors: Stefan Engel, Wörrstadt; Joachim Rheinheimer, Ludwigshafen; Ernst Baumann, Dudenhofen; Wolfgang von Deyn, Neustadt; Regina Luise Hill, Speyer; Guido Mayer; Ulf Misslitz, both of Neustadt; Oliver Wagner, Ludwigshafen; Matthias Witschel, Ludwigshafen; Martina Otten, Ludwigshafen; Helmut Walter, Obrigheim; Karl-Otto Westphalen, Speyer, all of Germany

[73] Assignee: BASF Aktiengesellschaft, Ludwigshafen, Germany

[21] Appl. No.: 09/485,232

[22] PCT Filed: Jul. 20, 1998

[86] PCT No.: PCT/EP98/04481

§ 371 Date: Feb. 7, 2000

§ 102(e) Date: Feb. 7, 2000

[87] PCT Pub. No.: WO99/07697

PCT Pub. Date: Feb. 18, 1999

[30] Foreign Application Priority Data

Aug. 7, 1997 [DE] Germany .......................... 197 34 186

[51] Int. Cl.⁷ ........................ A01N 43/56; C07D 403/10; C07D 407/10

[52] U.S. Cl. ............................ 504/282; 544/96; 544/182; 544/215; 544/238; 544/333; 544/405; 546/276.1; 548/110; 548/128; 548/131; 548/136; 548/143; 548/203; 548/204; 548/214; 548/240; 548/247; 548/255; 548/266.2; 548/364.1; 548/365.1; 548/365.7; 548/312.4

[58] Field of Search .................. 548/365.7, 364.1, 548/365.1; 504/282

[56] References Cited

U.S. PATENT DOCUMENTS 3,655,693  4/1972  Shen.
5,846,907  12/1998  von Deyn et al..

FOREIGN PATENT DOCUMENTS 282 944     9/1988  European Pat. Off..
282 944 A3  9/1988  European Pat. Off..

OTHER PUBLICATIONS

Chem Ber. 105, 863–873 (1972) Bohlmann et al.
Chem. Abs. Vo. 076 (1972) No. 15, 85658n.
XP–002088290, Miyano et al., 1909–1912.

*Primary Examiner*—Robert W. Ramsuer
*Attorney, Agent, or Firm*—Keil & Weinkauf

[57] ABSTRACT

4-Benzoylpyrazoles of the formula I

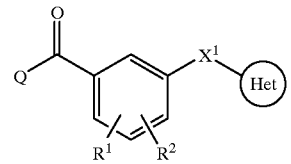

useful for controlling harmful plants, are disclosed.

9 Claims, No Drawings

SUBSTITUTED 4-BENZOYLPYRAZOLES

This application is a 371 of PCT/EP98/04481 filed Jul. 20, 1998.

The present invention relates to substituted 4-benzoylpyrazoles of the formula I

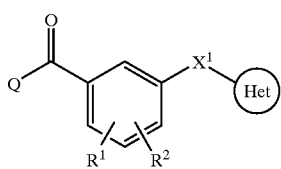

I where:
- $R^1$ and $R^2$ are each hydrogen, mercapto, nitro, halogen, cyano, thiocyanato, $C_1$–$C_6$-alkyl, $C_1$–$C_6$-haloalkyl, $C_1$–$C_6$-alkoxy, $C_2$–$C_6$-alkenyl, $C_2$–$C_6$-alkynyl, —$OR^3$, —$OCOR^3$, —$OSO_2R^3$, —$S(O)_nR^3$, —$SO_2OR^3$, —$SO_2N(R^3)_2$, —$NR^3SO_2R^3$ or —$NR^3COR^3$;
- $R^3$ is hydrogen, $C_1$–$C_6$-alkyl, $C_1$–$C_6$-haloalkyl, $C_2$–$C_6$-alkenyl, $C_2$–$C_6$-alkynyl, phenyl or phenyl-$C_1$–$C_6$-alkyl; where the alkyl radicals mentioned may be partially or fully halogenated and/or carry one to three of the following groups:
  - hydroxyl, mercapto, amino, cyano, $R^3$, —$OR^3$, —$SR^3$, —$N(R^3)_2$, =$NOR^3$, —$OCOR^3$, —$SCOR^3$, —$NR^3COR^3$, —$CO_2R^3$, —$COSR^3$, —$CON(R^3)_2$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the eight last-mentioned radicals may in turn be substituted;
- n is 0, 1 or 2;
- Q is a pyrazole of the formula II which is attached in position 4,

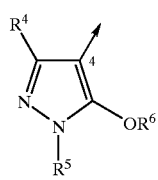

II where
- $R^4$ is hydrogen, $C_1$–$C_6$-alkyl or $C_1$–$C_6$-haloalkyl;
- $R^5$ is $C_1$–$C_6$-alkyl, $C_1$–$C_6$-haloalkyl, phenyl or phenyl which may be partially or fully halogenated and/or carry one to three of the following radicals:
  - nitro, cyano, $C_1$–$C_4$-alkyl, $C_1$–$C_4$-haloalkyl, $C_1$–$C_4$-alkoxy, $C_1$–$C_4$-haloalkoxy;
- $R^6$ is hydrogen, $C_1$–$C_6$-alkyl, $C_1$–$C_6$-haloalkyl, $C_1$–$C_6$-alkylcarbonyl, $C_1$–$C_6$-haloalkylcarbonyl, $C_1$–$C_6$-alkoxycarbonyl, $C_1$–$C_6$-alkylsulfonyl, $C_1$–$C_6$-haloalkylsulfonyl, phenylcarbonyl, phenylcarbonylmethyl, phenoxycarbonyl or phenylsulfonyl,
  where the four last-mentioned substituents are either unsubstituted, or the phenyl ring may in each case be partially or fully halogenated and/or carry one to three of the following radicals:
    nitro, cyano, $C_1$–$C_4$-alkyl, $C_1$–$C_4$-haloalkyl, $C_1$–$C_4$-alkoxy, $C_1$–$C_4$-haloalkoxy;
- $X^1$ is a straight-chain or branched $C_1$–$C_6$-alkylene, a $C_2$–$C_6$-alkenylene or a $C_2$–$C_6$-alkynylene chain, where the alkylene, alkenylene or alkynylene radicals mentioned may be partially halogenated and/or carry one to three of the following groups:
  —$OR^7$, —$OCOR^7$, —$OCONHR^7$ or —$OSO_2R^7$,
  and where those of the alkenylene radicals mentioned are excluded where the double bond is α,β to the phenyl ring and where Het is linked to the double bond via the β position;
- $R^7$ is hydrogen, $C_1$–$C_6$-alkyl, $C_2$–$C_6$-alkenyl, $C_2$–$C_6$-alkynyl, phenyl, phenyl-$C_1$–$C_6$-alkyl, where the alkyl, alkenyl or alkynyl radicals mentioned may be partially or fully halogenated and/or substituted by one or more of the following radicals:
  - hydroxyl, mercapto, amino, cyano, nitro, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy;
- Het is a three- to six-membered, partially or fully saturated heterocyclic group or a three- to six-membered heteroaromatic group having up to three hetero atoms selected from the group consisting of:
  nitrogen, oxygen or sulfur,
  where the heterocyclic or heteroaromatic group mentioned may be partially or fully halogenated and/or substituted by $R^8$;
- $R^8$ is hydrogen, hydroxyl, mercapto, amino, cyano, nitro, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy, where in all instances each of the alkyl radicals may be substituted by one or more of the following radicals:
  cyano, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy;

and agriculturally useful salts thereof.

Moreover, the invention relates to processes and intermediates for preparing compounds of the formula I, to compositions comprising them and to the use of the compounds of the formula I and of compositions comprising them for controlling harmful plants.

The literature, for example EP-A 282 944, discloses 4-benzoylpyrazoles.

However, the herbicidal properties of the prior art compounds and their crop safety are not entirely satisfactory.

It is an object of the present invention to provide novel, in particular herbicidally active, compounds having improved properties.

We have found that this object is achieved by the 4-benzoylpyrazoles of the formula I according to the invention and their herbicidal activity.

Furthermore, we have found herbicidal compositions which comprise the compounds I and have very good herbicidal activity. Additionally, we have found processes for preparing these compositions and methods for controlling undesirable vegetation using the compounds I.

The present invention also provides stereoisomers of the compounds of the formula I. Both pure stereoisomers and mixtures are included.

Depending on the substitution pattern, the compounds of the formula I may contain one or more chiral centers, in which case they exist in the form of enantiomers or diastereomer mixtures. The invention provides both the pure enantiomers or diastereomers and mixtures thereof.

The compounds of the formula I may also be present in the form of their agriculturally useful salts, the kind of salt generally not being important. The salts of those cations or the acid addition salts of those acids whose cations or anions, respectively, do not adversely affect the herbicidal activity of the compounds I are generally suitable.

Suitable cations are in particular ions of the alkali metals, preferably lithium, sodium and potassium, of the alkaline earth metals, preferably calcium and magnesium, and of the transition metals, preferably manganese, copper, zinc and iron, and ammonium where, if desired, one to four hydrogen atoms may be replaced by $C_1$–$C_4$-alkyl or hydroxy-$C_1$–$C_4$-alkyl and/or one phenyl or benzyl, preferably diisopropylammonium, tetramethylammonium, tetrabutylammonium, trimethylbenzylammonium, furthermore phosphonium ions, sulfonium ions, preferably tri($C_1$–$C_4$-alkyl)sulfonium, and sulfoxonium ions, preferably tri($C_1$–$C_4$-alkyl)sulfoxonium.

Anions of useful acid addition salts are primarily chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and the anions of $C_1$–$C_4$-alkanoic acids, preferably formate, acetate, propionate and butyrate.

Process A

Reactions of pyrazoles of the formula II (where $R^6$=H) with an activated carboxylic acid IIIa or a carboxylic acid IIIb, which is preferably activated in situ, to give the acylation product V, and subsequent rearrangement to the compounds of the formula I according to the invention.

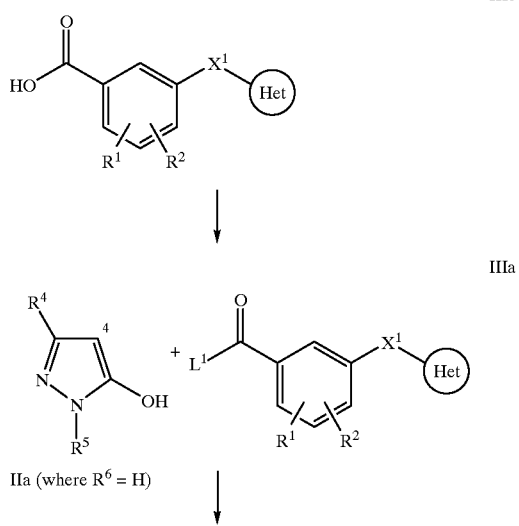

IIIb

IIIa

IIa (where $R^6$ = H)

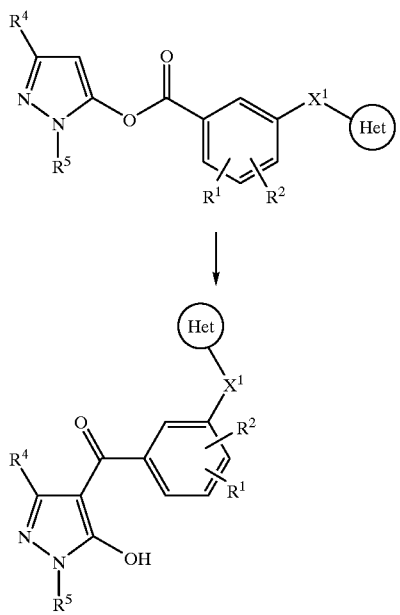

V

I $L^1$ is a nucleophilically replaceable leaving group such as halogen, for example bromine or chlorine, hetaryl, for example imidazolyl or pyridyl, or carboxylate, for example acetate, trifluoroacetate, etc.

The activated carboxylic acid can be employed directly, as in the case of the acyl halides, or be generated in situ, for example by using dicyclohexylcarbodiimide, triphenylphosphine/azodicarboxylic esters, 2-pyridine disulfite/triphenylphosphine, carbonyldiimidazole, etc.

It may be advantageous to carry out the acylation reaction in the presence of a base. Starting materials and auxiliary base are advantageously employed in equimolar amounts. A slight excess of auxiliary base, for example 1.2 to 1.5 mol equivalents, based on II, may be advantageous under certain circumstances.

Suitable auxiliary bases are tertiary alkylamines, pyridine or alkali metal carbonates. Examples of solvents which can be used are chlorinated hydrocarbons, such as methylene chloride, 1,2-dichloroethane, aromatic hydrocarbons, such as toluene, xylene, chlorobenzene, ethers, such as diethyl ether, methyl tert-butyl ether, tetrahydrofuran, dioxane, polar aprotic solvents, such as acetonitrile, dimethylformamide, dimethyl sulfoxide, or esters such as ethyl acetate or mixtures of these.

If acyl halides are employed as activated carboxylic acid component, it may be advantageous to cool the reaction mixture to 0–10° C. when adding this reaction partner. The mixture is subsequently stirred at 20–100° C., preferably at 25–50° C., until the reaction is complete. Work-up is carried out in the customary manner, for example by pouring the reaction mixture into water and extracting the product of value. Solvents which are particularly suitable for this purpose are methylene chloride, diethyl ether and ethyl acetate. After the organic phase has been dried and the solvent has been removed, the crude enol ester of the formula V is purified, preferably by chromatography. Alternatively, it is possible to employ the crude enol ester of the formula V without further purification for the rearrangement reaction.

The rearrangement of the enol esters of the formula V to the compounds of the formula I is advantageously carried out at from 20 to 40° C. in a solvent and in the presence of a base and, if appropriate, in the presence of a cyano compound.

Examples of solvents which can be used are acetonitrile, methylene chloride, 1,2-dichloroethane, dioxane, ethyl acetate, toluene or mixtures of these. Preferred solvents are acetonitrile and dioxane.

Suitable bases are tertiary amines such as triethylamine, pyridine or alkali metal carbonates, such as sodium carbonate, potassium carbonate, which are preferably employed in equimolar amounts or up to a four-fold excess, based on the ester.

Preference is given to using triethylamine or alkali metal carbonates.

Suitable cyano compounds are inorganic cyanides such as sodium cyanide, potassium cyanide and organic cyano compounds such as acetone cyanohydrin, trimethylsilyl cyanide. They are employed in an amount of 1 to 50 mol percent, based on the ester. Preference is given to using acetone cyanohydrin or trimethylsilyl cyanide, for example, in an amount of 5 to 15, preferably 10, mol percent, based on the ester.

Particular preference is given to employing alkali metal carbonates, such as potassium carbonate, in acetonitrile or dioxane.

Work-up can be carried out in a manner known per se. For example, the reaction mixture is acidified with dilute mineral acid, such as 5% strength hydrochloric acid or sulfuric acid, and extracted with an organic solvent, for example methylene chloride, ethyl acetate. The organic phase can be extracted with 5–10% strength alkali metal carbonate solution, for example sodium carbonate or potassium carbonate solution. The aqueous phase is acidified, and the precipitate which forms is filtered off with suction and/or extracted with methylene chloride or ethyl acetate, dried and concentrated.

(Examples of the synthesis of esters from hydroxypyrazoles and the rearrangement of the esters are mentioned, for example, in EP-A 282 944 or U.S. Pat. No. 4,643,757).

Process B

Reactions of 4-benzoylpyrazoles of the formula I (where $R^6$=H) with a compound of the formula IV (where $R^6 \neq$H):

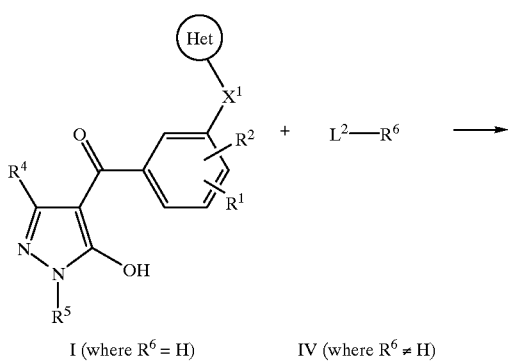

I (where $R^6$ = H)    IV (where $R^6 \neq$ H)

-continued

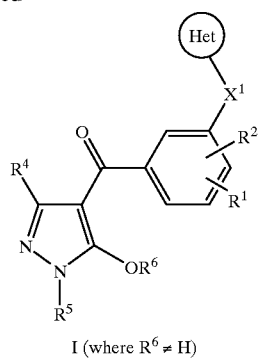

I (where $R^6 \neq$ H)

$L^2$ is a nucleophilically replaceable leaving group such as halogen, for example bromine, chlorine, hetaryl, for example imidazolyl, pyridyl, carboxylate, for example acetate, trifluoroacetate, sulfonate, for example mesylate, triflate, etc.

The compounds of the formula IV can be employed directly, for example in the case of the alkyl halides, acyl halides, sulfonyl halides, carboxylic anhydrides and sulfonic anhydrides, or prepared in situ, for example activated carboxylic acids (by means of carboxylic acid and dicyclohexylcarbodiimide, carbonyldiimidazole, etc.).

In general, the starting materials are employed in an equimolar ratio. However, it may also be advantageous to employ an excess of one or the other component.

Where appropriate, it may be advantageous to carry out the reaction in the presence of a base. The starting materials and the auxiliary base are advantageously employed in equimolar amounts. Under certain circumstances, it may be advantageous to employ an excess of the auxiliary base, for example 1.5 to 3 mol equivalents, based on Ia.

Suitable auxiliary bases are tertiary alkylamines such as triethylamine, pyridine, alkali metal carbonates, for example sodium carbonate, potassium carbonate, and alkali metal hydrides, for example sodium hydride. Preference is given to using triethylamine, pyridine and potassium carbonate.

Examples of suitable solvents are chlorinated hydrocarbons such as methylene chloride, 1,2-dichloroethane, aromatic hydrocarbons, for example toluene, xylene, chlorobenzene, ethers, such as diethyl ether, methyl tert-butyl ether, tetrahydrofuran, dioxane, polar aprotic solvents, such as acetonitrile, dimethylformamide, dimethyl sulfoxide or esters, such as ethyl acetate, or mixtures of these.

The reaction temperature is generally in the range of from 0° C. to the boiling point of the reaction mixture.

Work-up can be carried out in a manner known per se.

The benzoic acids of the formula III are novel,

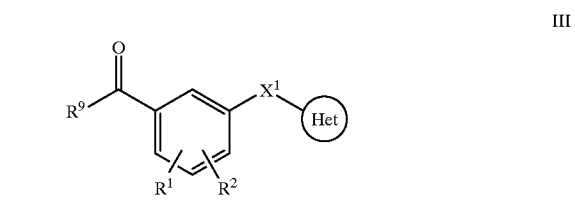

III the variables being defined as follows:
$R^1$ and $R^2$ are each hydrogen, mercapto, nitro, halogen, cyano, thiocyanato, $C_1$–$C_6$-alkyl, $C_1$–$C_6$-haloalkyl, $C_1$–$C_6$-alkoxy, $C_2$–$C_6$-alkenyl, $C_2$–$C_6$-alkynyl, —$OR^3$, —$OCOR^3$, —$OSO_2R^3$, —$S(O)_nR^3$, —$SO_2OR^3$, —$SO_2N(R^3)_2$, —$NR^3SO_2R^3$ or —$NR^3COR^3$;

$R^3$ is hydrogen, $C_1$–$C_6$-alkyl, $C_1$–$C_6$-haloalkyl, $C_2$–$C_6$-alkenyl, $C_2$–$C_6$-alkynyl, phenyl or phenyl-$C_1$–$C_6$-alkyl; where the alkyl radicals mentioned may be partially or fully halogenated and/or carry one to three of the following groups:
hydroxyl, mercapto, amino, cyano, $R^3$, —$OR^3$, —$SR^3$, —$N(R^3)_2$, =$NOR^3$, —$OCOR^3$, —$SCOR^3$, —$NR^3COR^3$, —$CO_2R^3$, —$COSR^3$, —$CON(R^3)_2$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the eight last-mentioned radicals may in turn be substituted;

n is 0, 1 or 2;

$X^1$ is a straight-chain or branched $C_1$–$C_6$-alkylene, a $C_2$–$C_6$-alkenylene or a $C_2$–$C_6$-alkynylene chain, where the alkyl, alkenyl or alkynyl radicals mentioned may be partially halogenated and/or carry one to three of the following groups:
—$OR^7$, —$OCOR^7$, —$OCONHR^7$ or —$OSO_2R^7$,
and where those of the alkenylene radicals mentioned are excluded where the double bond is α,β to the phenyl ring and where Het is linked to the double bond via the β position.

$R^7$ is hydrogen, $C_1$–$C_6$-alkyl, $C_2$–$C_6$-alkenyl, $C_2$–$C_6$-alkynyl, phenyl, phenyl-$C_1$–$C_6$-alkyl, where the alkyl, alkenyl or alkynyl radicals mentioned may be partially or fully halogenated and/or substituted by one or more of the following radicals:
hydroxyl, mercapto, amino, cyano, nitro, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy;

Het is a three to six-membered, partially or fully saturated heterocyclic group or a three to six-membered heteroaromatic group having up to three hetero atoms selected from the group consisting of:
nitrogen, oxygen or sulfur,
where the heterocyclic or heteroaromatic group mentioned may be partially or fully halogenated and/or substituted by $R^8$;

$R^8$ is hydrogen, hydroxyl, mercapto, amino, cyano, nitro, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy, where in all instances each of the alkyl radicals may be substituted by one or more of the following radicals:
cyano, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy;

$R^9$ is hydroxyl or a hydrolyzable radical.

Examples of hydrolyzable radicals are alkoxy, phenoxy, alkylthio, phenylthio radicals with or without substitution, halides, hetaryl radicals which are attached via nitrogen, amino, imino radicals with or without substitution, etc.

Preference is given to benzoyl halides IIIa where $L^1$=halogen ($\triangleq$ III where $R^9$=halogen),

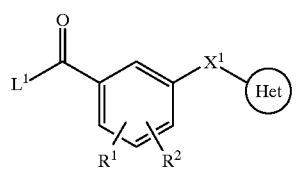

IIIa where the variables $R^1$, $R^2$, $X^1$ and Het are each as defined under formula III and $L^1$ is halogen, in particular chlorine or bromine.

Likewise, preference is given to benzoic acids of the formula IIIb ($\triangleq$ III where $R^9$=hydroxyl),

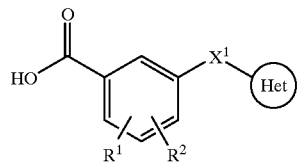

IIIb where the variables $R^1$, $R^2$, $X^1$ and Het are each as defined under formula III.

Likewise, preference is given to benzoic esters of the formula IIIc ($\triangleq$ III where $R^9$=$C_1$–$C_6$-alkoxy),

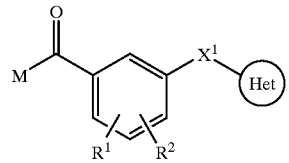

IIIc where the variables $R^1$, $R^2$, $X^1$ and Het are each as defined under formula III and M is $C_1$–$C_6$-alkoxy.

The compounds of the formula IIIa (where $L^1$=halogen) can be prepared similarly to methods known from the literature (cf. L. G. Fieser, M. Fieser "Reagents for Organic Synthesis", Vol. I, p. 767–769 (1967)) by reacting benzoic acids of the formula IIIb with halogenating agents such as thionyl chloride, thionyl bromide, phosgene, diphosgene, triphosgene, oxalyl chloride, oxalyl bromide.

The benzoic acids of the formula IIIb can be obtained inter alia by hydrolysis of the benzoic esters of the formula IIIc (where M=$C_1$–$C_6$-alkoxy).

The benzoic esters of the formula IIIc according to the invention are preparable by various methods known from the literature (for example a. G. Dittus in Houben-Weyl, Methoden der Organischen Chemie, Volume VI/3, Sauerstoff-Verbindungen I, 4th edition, p. 493 ff., Georg Thieme Verlag, 1965; b. T. L. Gilchrist, Heterocyclenchemie, 2nd edition, Verlag Chemie, 1995), and illustrated in the examples below.

Process C

Metallation of suitable benzoic esters IIIc ortho to the ester function using strong, organometallic bases, and subsequent 1,2-addition of a carbonyl compound V affords the benzoic esters IIIe according to the invention,

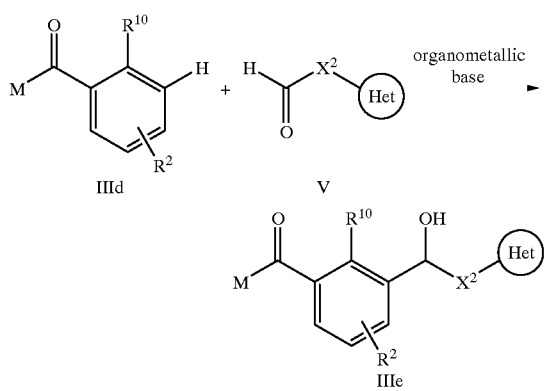

where $R^{10}$ is a substituent $R^1$ suitable for ortho metallation (for example V. Snieckus, *Chem. Rev.*, 1990, 90, 879), preferably halogen and $C_1$–$C_6$-alkoxy and $X^2$ is a straight-chain or branched $C_1$–$C_5$-alkylene, a $C_2$–$C_5$-alkenylene or a $C_2$–$C_5$-alkynylene chain, where the alkylene, alkenylene or alkynylene radicals mentioned may be partially halogenated and/or carry one to three of the following groups:
—$OR^7$, —$OCOR^7$, —$OCONHR^7$ or —$OSO_2R^7$.

Organometallic bases which are suitable for ortho-metallation of the benzoic esters IIId known from the literature are, for example, alkyllithium compounds, preferably n-butyllithium or sec-butyllithium, lithium dialkylamides, preferably lithium diisopropylamide or sodium hexamethyldisilazide.

Suitable inert solvents for the direct ortho-metallation are, for example, tetrahydrofuran, diethyl ether, 1,2-dimethoxyethane or 1,4-dioxane, dimethylformamide, dimethyl sulfoxide, methyl tert-butyl ether or else mixtures of these solvents.

The reaction temperatures may be from −80 to 100° C., preferably from −80 to 40° C.

The reaction of the ortho-metallated benzoic esters IIId, which are generated in situ, with the aldehydes V is carried out at from −80 to 100° C.

The products IIIe according to the invention contain a hydroxymethylene group which is suitable for further derivatizations by methods known from the literature. Thus, the hydroxymethylene group can, for example, be methylated to the methoxy group.

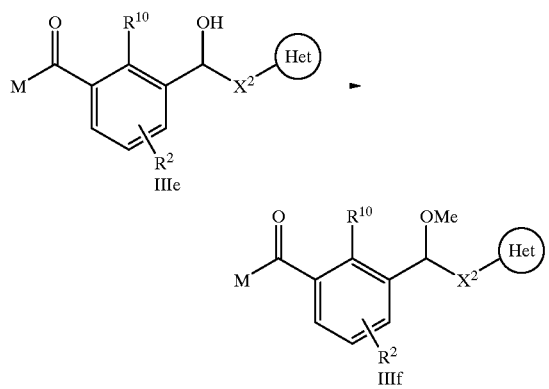

Process D 1,3-dipolar cycloaddition of the benzoic esters IIIg with olefins or acetylenes with or without substitution under dehydrating conditions affords the benzoic esters according to the invention, for example IIIh.

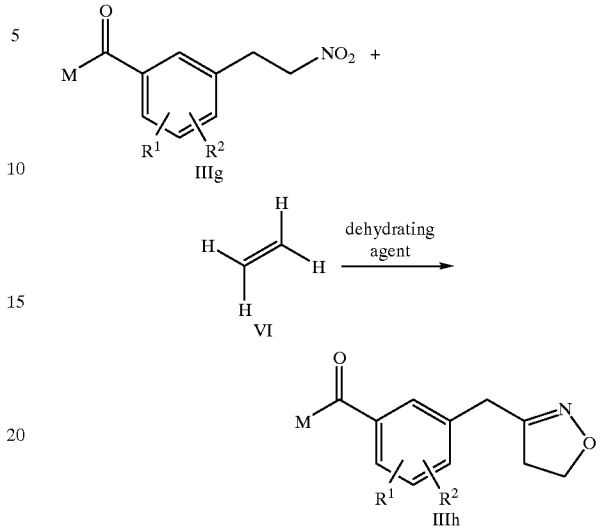

The dehydration according to the method of Mukaiyama is preferably carried out using aromatic isocyanates (for example T. Mukaiyama et al., *J. Am. Chem. Soc.* 1960, 82, 5339), for example phenyl isocyanate or 4-chlorophenyl isocyanate.

In the variant according to Shimizu, aliphatic chloroformates (for example T. Shimizu et al., *Bull. Chem. Soc. Jpn.* 1986, 59, 2827), preferably ethyl chloroformate, can also be used.

More recent developments show that, for example, N,N-diethylaminosulfur trifluoride (DAST), (methoxycarbonylsulfamoyl)triethylammonium hydroxide (Burgess Reagent), phosphoryl chloride (for example C. Mioskowski et al., *Tetrahedron Letters* 1997, 38, 1547) or else a combination of di-tert-butyl dicarbonate ($Boc_2O$) and 4-dimethylaminopyridine (DMAP) (A. Hassner et al., *Synthesis* 1997, 309) can likewise be employed successfully as dehydrating agents for the generation of nitrile oxides.

The nitrile oxides formed in this manner in situ can be reacted at from room temperature to the boiling point of the solvent used with any substituted olefins or acetylene to give the benzoic esters IIIc according to the invention, $X^1$ in this case being, for example, a methylene group and Het an isoxazole or isoxazoline skeleton with or without substitution.

The cycloaddition is carried out in inert solvents, for example toluene, chloroform or acetonitrile.

The benozoic ester IIIg can be obtained by reduction according to methods known from the literature from IIIj, which is preparable by nitroolefination (for example a. V. V. Perekalin et al., Nitroalkenes, John Wiley & Sons Ltd., New York 1994, b. A. G. M. Barrett et al., *Chem. Rev.* 1986, 86, 751) of the corresponding aldehyde IIIi.

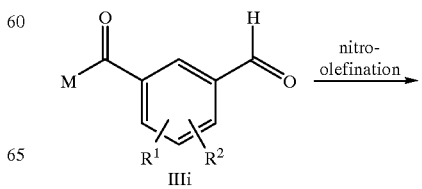

-continued

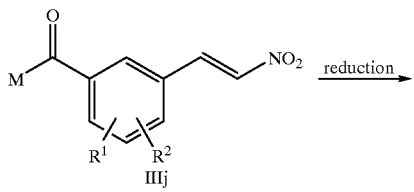
IIIj reduction

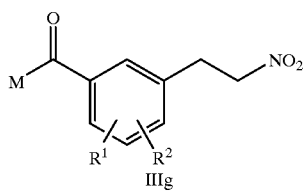
IIIg

Preference is given to compounds of the formula I according to the invention where the group $X^1$ is either a $C_1$–$C_2$-alkylene or a $C_2$-alkenylene chain and
Het is a three- to six-membered, partially or fully saturated heterocyclic group or a three- to six-membered heteroaromatic group having up to three hetero atoms selected from the group consisting of:
nitrogen, oxygen and sulfur,
where the heterocyclic or heteroaromatic group mentioned may be partially or fully halogenated and/or may be substituted by $R^8$.

In addition, preference is given to compounds of the formula I according to the invention where the group Het is a five- or six-membered, partially or fully saturated heterocyclic or a five- or six-membered heteroaromatic group having up to three hetero atoms selected from the group consisting of nitrogen, oxygen and sulfur, where the heterocyclic or heteroaromatic group mentioned may be partially or fully halogenated and/or substituted by $R^8$;

$R^8$ is hydrogen, hydroxyl, mercapto, amino, cyano, nitro, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy, where in all instances each of the alkyl radicals may be substituted by one or more of the following radicals:
cyano, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy.

The organic moieties mentioned for the substituents $R^1$–$R^{10}$ or as radicals on phenyl, hetaryl and heterocyclyl rings are collective terms for individual enumerations of the individual group members. All hydrocarbon chains, ie. all alkyl, haloalkyl, cycloalkyl, alkoxyalkyl, alkoxy, haloalkoxy, alkyliminooxy, alkoxyamino, alkylsulfonyl, haloalkylsulfonyl, alkylcarbonyl, haloalkylcarbonyl, alkoxycarbonyl, alkoxyalkoxycarbonyl, alkenyl, cycloalkenyl, alkynyl moieties can be straight-chain or branched. Unless otherwise specified, halogenated substituents preferably have attached to them one to five identical or different halogen atoms, the meaning of halogen being in each case fluorine, chlorine, bromine or iodine.

Examples of other meanings are:
$C_1$–$C_4$-alkyl, and the alkyl moieties of $C_1$–$C_4$-alkylcarbonyl: methyl, ethyl, n-propyl, 1-methylethyl, butyl, 1-methylpropyl, 2-methylpropyl and 1,1-dimethylethyl;

$C_1$–$C_6$-alkyl and the alkyl moieties of $C_1$–$C_6$-alkoxy-$C_1$–$C_6$-alkyl and $C_1$–$C_6$-alkylcarbonyl: $C_1$–$C_4$-alkyl as mentioned above, and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$–$C_4$-haloalkyl: a $C_1$–$C_4$-alkyl radical as mentioned above which is partially or fully substituted by fluorine, chlorine, bromine and/or iodine, e.g. chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$–$C_6$-haloalkyl and the haloalkyl moieties of $C_1$–$C_6$-haloalkylcarbonyl: $C_1$–$C_4$-haloalkyl as mentioned above, and also 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_1$–$C_4$-alkoxy and the alkoxy moieties of $C_1$–$C_4$-alkoxyamino, $C_1$–$C_4$-alkoxy-$C_2$–$C_6$-alkoxycarbonyl and $C_1$–$C_4$-alkoxycarbonyl: methoxy, ethoxy, propoxy, 1-methylethoxy, butoxy, 1-methylpropoxy, 2-methylpropoxy and 1,1-dimethylethoxy;

$C_1$–$C_6$-alkoxy and the alkoxy moieties of $C_1$–$C_6$-alkoxy-$C_1$–$C_6$-alkyl, $C_1$–$C_6$-alkoxy-$C_2$–$C_6$-alkyl, $C_1$–$C_4$-alkoxy-$C_2$–$C_6$-alkoxycarbonyl and $C_1$–$C_6$-alkoxycarbonyl: $C_1$–$C_4$-alkoxy as mentioned above, and also pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, e.g. fluoromethoxy, difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$–$C_4$-alkylsulfonyl ($C_1$–$C_4$-alkyl-S(=O)$_2$—): methylsulfonyl, ethylsulfonyl, propylsulfonyl, 1-methylethylsulfonyl, butylsulfonyl, 1-methylpropylsulfonyl, 2-methylpropylsulfonyl and 1,1-dimethylethylsulfonyl;

$C_1$–$C_6$-alkylsulfonyl: $C_1$–$C_4$-alkylsulfonyl as mentioned above, and also pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, 1,1-dimethylpropylsulfonyl, 1,2-dimethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

$C_1$–$C_6$-haloalkylsulfonyl: a $C_1$–$C_6$-alkylsulfonyl radical as mentioned above which is partially or fully substituted by fluorine, chlorine, bromine and/or iodine, ie. fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2,2,2-trichloroethylsulfonyl, 2-chloro-2-fluoroethylsulfonyl, 2-chloro-2,2-difluoroethylsulfonyl, 2,2-dichloro-2-fluoroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl, nonafluorobutylsulfonyl, 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl and dodecafluorohexylsulfonyl;

$C_1$–$C_4$-alkyliminooxy: methyliminooxy, ethyliminooxy, 1-propyliminooxy, 2-propyliminooxy, 1-butyliminooxy and 2-butyliminooxy;

$C_3$–$C_6$-alkenyl: prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl, 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl; p1 $C_2$–$C_6$-alkenyl: $C_3$–$C_6$-alkenyl as mentioned above, and also ethenyl;

$C_3$–$C_6$-alkynyl: prop-1-yn-1-yl, prop-2-yn-1-yl, but-1-yn-1-yl, but-1-yn-3-yl, but-1-yn-4-yl, but-2-yn-1-yl, pent-1-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-1-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl;

$C_2$–$C_6$-alkynyl: $C_3$–$C_6$-alkynyl as mentioned above, and also ethynyl;

$C_3$–$C_6$-cycloalkyl: cyclopropyl, cyclobutyl, cyclopentyl and cyclohexyl;

$C_4$–$C_6$-cycloalkenyl: cyclobuten-1-yl, cyclobuten-3-yl, cyclopenten-1-yl, cyclopenten-3-yl, cyclopenten-4-yl, cyclohexen-1-yl, cyclohexen-3-yl and cyclohexen-4-yl;

heterocyclyl, and also the heterocyclyl radicals in heterocyclyloxy: three- to seven-membered saturated or partially unsaturated mono- or polycyclic heterocycles which contain one to three hetero atoms selected from a group consisting of oxygen, nitrogen and sulfur, such as oxiranyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4- oxadiazolidin-2-yl, 1,3,4-thiadiazolidin-2-yl, 1,3,4-triazolidin-2-yl, 2,3-dihydrofuran-2-yl, 2,3-dihydrofuran-3-yl, 2,3-dihydrofuran-4-yl, 2,3-dihydrofuran-5-yl, 2,5-dihydrofuran-2-yl, 2,5-dihydrofuran-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroxazol-5-yl, 2,3-dihydroisothiazol-3-yl, 2,3-dihydroisothiazol-4-yl, 2,3-dihydroisothiazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol -5-yl, 2,3-dihydropyrazol-3-yl, 2,3-dihydropyrazol-4-yl, 2,3-dihydropyrazol-5-yl, 4,5-dihydropyrazol-3-yl, 4,5-dihydropyrazol-4-yl, 4,5-dihydropyrazol-5-yl, 2,5-dihydropyrazol-3-yl, 2,5-dihydropyrazol-4-yl, 2,5-dihydropyrazol-5-yl, 2,3-dihydrooxazol-2-yl, 2,3-dihydrooxazol-4-yl, 2,3-dihydrooxazol-5-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, 2-tetrahydropyranyl, 3-tetrahydropyranyl, 4-tetrahydropyranyl, 2-tetrahydrothiopyranyl, 3-tetrahydrothiopyranyl, 4-tetrahydrothiopyranyl, 1,3-dioxolan-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl, hetaryl, and also the hetaryl radicals in hetaryloxy:
aromatic mono- or polycyclic radicals which, besides carbon ring members, may additionally contain one to four nitrogen atoms or one to three nitrogen atoms and one oxygen or one sulfur atom or one oxygen or one sulfur atom, e.g. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4,5-tetrazin-3-yl, and also the corresponding benzo-fuzed derivatives.

All phenyl, hetaryl and heterocyclyl rings are preferably unsubstituted or have attached to them one to three halogen atoms and/or one or two radicals selected from the following group: nitro, cyano, methyl, trifluoromethyl, methoxy, trifluoromethoxy or methoxycarbonyl.

With a view to the use of the compounds of the formula I according to the invention as herbicides, the variables preferably have the following meanings, viz. in each case alone or in combination:

$R^1$ is nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^3$ or —$S(O)_nR^3$;
particularly preferably nitro, halogen such as fluorine, chlorine or bromine, $C_1$–$C_6$-haloalkyl, —$OR^3$ or —$SO_2R^3$;

$R^2$ is hydrogen, nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^3$ or —$S(O)_nR^3$;
particularly preferably hydrogen, nitro, halogen such as fluorine, chlorine or bromine, $C_1$–$C_6$-alkyl, $C_1$–$C_6$-haloalkyl, —$OR^3$ or —$SO_2R^3$;

$R^3$ is hydrogen, $C_1$–$C_6$-alkyl, $C_1$–$C_6$-haloalkyl, $C_2$–$C_6$-alkenyl, $C_2$–$C_6$-alkynyl, phenyl or phenyl-$C_1$–$C_6$-alkyl;
particularly preferably hydrogen, $C_1$–$C_4$-alkyl, $C_1$–$C_4$-haloalkyl, $C_2$–$C_3$-alkenyl, $C_2$–$C_3$-alkynyl or phenyl; where the alkyl radicals mentioned may be partially or fully halogenated and/or may carry one to three of the following groups:
hydroxyl, mercapto, amino, cyano, $R^3$, —$OR^3$, —$SR^3$, —$N(R^3)_2$, =$NOR^3$, —$OCOR^3$, —$SCOR^3$, —$NR^3COR^3$, —$CO_2R^3$, —$COSR^3$, —$CON(R^3)_2$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the eight last-mentioned radicals may in turn be substituted;

n is 0, 1 or 2, particularly preferably 0 or 2;

$R^4$ is hydrogen, $C_1$–$C_6$-alkyl or $C_1$–$C_6$-haloalkyl; particularly preferably hydrogen, methyl, ethyl or trifluoromethyl;

$R^5$ is $C_1$–$C_6$-alkyl or $C_1$–$C_6$-haloalkyl; particularly preferably methyl, ethyl, propyl, isopropyl, butyl or isobutyl;

$R^6$ is hydrogen, $C_1$–$C_6$-alkyl, $C_1$–$C_6$-alkylcarbonyl, $C_1$–$C_6$-haloalkylcarbonyl, $C_1$–$C_6$-alkoxycarbonyl, $C_1$–$C_6$-alkylsulfonyl, $C_1$–$C_6$-haloalkylsulfonyl, phenylcarbonylmethyl or phenylsulfonyl, where the phenyl ring of the two last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy;

$X^1$ is a straight-chain or branched $C_1$–$C_4$-alkylene, a propenylene or butenylene or a $C_2$–$C_4$-alkynylene chain, particularly preferably a methylene, ethylene, propylene, propenylene, ethynylene or propynylene chain, where the alkylene, alkenylene or alkynylene radicals mentioned may be partially halogenated and/or may carry one to three of the following groups:
—$OR^7$, —$OCOR^7$, —$OCONHR^7$ or —$OSO_2R^7$, and where those of the alkenylene radicals mentioned are excluded where the double bond is α,β to the phenyl ring and where Het is linked to the double bond via the β position;

R$^7$ is hydrogen, $C_1$–$C_4$-alkyl, $C_2$–$C_4$-alkenyl, $C_2$–$C_4$-alkynyl, phenyl, phenyl-$C_1$–$C_4$-alkyl, where the alkyl, alkenyl or alkynyl radicals mentioned may be partially or fully halogenated and/or may be substituted by one or more of the following radicals:
  hydroxyl, mercapto, amino, cyano, nitro, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy;

R$^8$ is hydrogen, hydroxyl, mercapto, amino, cyano, nitro, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy, where in all instances each of the alkyl radicals may be substituted by one or more of the following radicals:
  cyano, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy.

Particular preference is given to compounds of the formula Ia where R$^1$ is attached in position 2 and R$^2$ is attached in position 4 of the phenyl ring.

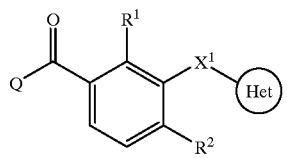

Ia

Very particular preference is given to the compounds of the formula Ia in which the substituents R$^1$ and R$^2$ and Q are each as defined above, X$^1$ is a $C_1$–$C_2$-alkylene or a $C_2$-alkynylene chain and
  Het is a three- to six-membered, partially or fully saturated heterocyclic group or a three- to six-membered heteroaromatic group having up to three hetero atoms selected from the group consisting of:
  nitrogen, oxygen and sulfur,
  where the heterocyclic or heteroaromatic group mentioned may be partially or fully halogenated and/or may be substituted by R$^8$.

Additionally, very particular preference is given to the compounds of the formula Ia according to the invention in which the substituents R$^1$, R$^2$, Q and X$^1$ are each as defined above and Het is a five- or six-membered, partially or fully saturated heterocyclic or a five- or six-membered heteroaromatic group having up to three hetero atoms selected from the group consisting of
  nitrogen, oxygen and sulfur.

Particular preference is given to the compounds Ib of Tables 1 to 144.

TABLE A

| No. | X$^1$ | Het |
|---|---|---|
| 1 | CH$_2$ | oxiranyl |
| 2 | CH$_2$ | 3-methyl-2-oxiranyl |
| 3 | CH$_2$ | 2-oxetanyl |
| 4 | CH$_2$ | 3-hydroxy-3-methyl-2-oxetanyl |
| 5 | CH$_2$ | 3-hydroxy-3-ethyl-2-oxetanyl |
| 6 | CH$_2$ | 3-hydroxy-3-propyl-2-oxetanyl |
| 7 | CH$_2$ | 3-hydroxy-3-butyl-2-oxetanyl |
| 8 | CH$_2$ | 3-methoxy-3-methyl-2-oxetanyl |
| 9 | CH$_2$ | 3-methoxy-3-ethyl-2-oxetanyl |
| 10 | CH$_2$ | 3-methoxy-3-propyl-2-oxetanyl |
| 11 | CH$_2$ | 3-methoxy-3-butyl-2-oxetanyl |
| 12 | CH$_2$ | 3-trimethylsilyloxy-3-methyl-2-oxetanyl |
| 13 | CH$_2$ | 3-trimethylsilyloxy-3-ethyl-2-oxetanyl |
| 14 | CH$_2$ | 3-trimethylsilyloxy-3-propyl-2-oxetanyl |
| 15 | CH$_2$ | 3-trimethylsilyloxy-3-butyl-2-oxetanyl |
| 16 | CH$_2$ | 3-oxetanyl |
| 17 | CH$_2$ | 2-furyl |
| 18 | CH$_2$ | 4,5-dihydro-2-furyl |
| 19 | CH$_2$ | 2,3-dihydro-2-furyl |
| 20 | CH$_2$ | 3-furyl |
| 21 | CH$_2$ | 4,5-dihydro-3-furyl |
| 22 | CH$_2$ | 2,3-dihydro-3-furyl |
| 23 | CH$_2$ | 2-thienyl |
| 24 | CH$_2$ | 4,5-dihydro-2-thienyl |
| 25 | CH$_2$ | 2,3-dihydro-2-thienyl |
| 26 | CH$_2$ | 5-chloro-2-thienyl |
| 27 | CH$_2$ | 5-methyl-2-thienyl |
| 28 | CH$_2$ | 3-thienyl |
| 29 | CH$_2$ | 4,5-dihydro-3-thienyl |
| 30 | CH$_2$ | 2,3-dihydro-3-thienyl |
| 31 | CH$_2$ | 2-pyrrolyl |
| 32 | CH$_2$ | 2,5-dihydro-2-pyrrolyl |
| 33 | CH$_2$ | 3-pyrrole |
| 34 | CH$_2$ | 2,5-dihydro-3-pyrrolyl |
| 35 | CH$_2$ | 3-isoxazolyl |
| 36 | CH$_2$ | 4-methyl-3-isoxazolyl |
| 37 | CH$_2$ | 5-methyl-3-isoxazolyl |
| 38 | CH$_2$ | 4,5-dimethyl-3-isoxazolyl |
| 39 | CH$_2$ | 4,5-dihydro-3-isoxazolyl |
| 40 | CH$_2$ | 4-methyl-4,5-dihydro-3-isoxazolyl |
| 41 | CH$_2$ | 5-methyl-4,5-dihydro-3-isoxazolyl |
| 42 | CH$_2$ | 4,5-dimethyl-4,5-dihydro-3-isoxazolyl |
| 43 | CH$_2$ | 4-isoxazolyl |
| 44 | CH$_2$ | 3-methyl-4-isoxazolyl |
| 45 | CH$_2$ | 5-methyl-4-isoxazolyl |
| 46 | CH$_2$ | 5-cyclopropyl-4-isoxazolyl |
| 47 | CH$_2$ | 5-phenyl-4-isoxazolyl |
| 48 | CH$_2$ | 3,5-dimethyl-4-isoxazolyl |
| 49 | CH$_2$ | 4,5-dihydro-4-isoxazolyl |
| 50 | CH$_2$ | 3-methyl-4,5-dihydro-4-isoxazolyl |
| 51 | CH$_2$ | 5-methyl-4,5-dihydro-4-isoxazolyl |
| 52 | CH$_2$ | 3,5-dimethyl-4,5-dihydro-4-isoxazolyl |
| 53 | CH$_2$ | 5-isoxazolyl |
| 54 | CH$_2$ | 3-methyl-5-isoxazolyl |
| 55 | CH$_2$ | 4-methyl-5-isoxazolyl |
| 56 | CH$_2$ | 3,4-dimethyl-5-isoxazolyl |
| 57 | CH$_2$ | 4,5-dihydro-5-isoxazolyl |
| 58 | CH$_2$ | 3-methyl-4,5-dihydro-5-isoxazolyl |
| 59 | CH$_2$ | 4-methyl-4,5-dihydro-5-isoxazolyl |
| 60 | CH$_2$ | 3,4-dimethyl-4,5-dihydro-5-isoxazolyl |
| 61 | CH$_2$ | 3-isothiazolyl |
| 62 | CH$_2$ | 4-methyl-3-isothiazolyl |
| 63 | CH$_2$ | 5-methyl-3-isothiazolyl |
| 64 | CH$_2$ | 4-isothiazolyl |
| 65 | CH$_2$ | 3-methyl-4-isothiazolyl |
| 66 | CH$_2$ | 5-methyl-4-isothiazolyl |
| 67 | CH$_2$ | 5-isothiazolyl |
| 68 | CH$_2$ | 3-methyl-5-isothiazolyl |
| 69 | CH$_2$ | 4-methyl-5-isothiazolyl |
| 70 | CH$_2$ | 2-oxazolyl |
| 71 | CH$_2$ | 4-oxazolyl |
| 72 | CH$_2$ | 5-oxazolyl |
| 73 | CH$_2$ | 2-thiazolyl |
| 74 | CH$_2$ | 4-thiazolyl |
| 75 | CH$_2$ | 5-thiazolyl |
| 76 | CH$_2$ | 3-pyrazolyl |
| 77 | CH$_2$ | 4-pyrazolyl |

TABLE A-continued

| No. | X¹ | Het |
|---|---|---|
| 78 | CH₂ | 1-methyl-3-pyrazolyl |
| 79 | CH₂ | 1-methyl-4-pyrazolyl |
| 80 | CH₂ | 1-methyl-5-pyrazolyl |
| 81 | CH₂ | 2-imidazolyl |
| 82 | CH₂ | 1-methyl-2-imidazolyl |
| 83 | CH₂ | 5-methyl-[1,3,4]-2-oxadiazolyl |
| 84 | CH₂ | 5-methyl-[1,2,4]-3-oxadiazolyl |
| 85 | CH₂ | 5-methyl-[1,3,4]-2-thiadiazolyl |
| 86 | CH₂ | 5-methyl-[1,2,4]-3-thiadiazolyl |
| 87 | CH₂ | [1,2,4]-3-triazolyl |
| 88 | CH₂ | [1,2,3]-4-triazolyl |
| 89 | CH₂ | 2-pyridyl |
| 90 | CH₂ | 6-chloro-2-pyridyl |
| 91 | CH₂ | 6-methoxy-2-pyridyl |
| 92 | CH₂ | 6-trifluoromethyl-2-pyridyl |
| 93 | CH₂ | 3-pyridyl |
| 94 | CH₂ | 2-chloro-3-pyridyl |
| 95 | CH₂ | 2-methoxy-3-pyridyl |
| 96 | CH₂ | 4-pyridyl |
| 97 | CH₂ | 2-chloro-4-pyridyl |
| 98 | CH₂ | 2-methoxy-4-pyridyl |
| 99 | CH₂ | 2-ethoxy-4-pyridyl |
| 100 | CH₂ | 2-methylthio-4-pyridyl |
| 101 | CH₂ | 2-trifluoromethyl-5-pyridyl |
| 102 | CH₂ | 2-pyrimidinyl |
| 103 | CH₂ | 3-pyrimidinyl |
| 104 | CH₂ | 4-pyrimidinyl |
| 105 | CH₂ | 2-pyrazinyl |
| 106 | CH₂ | 3-pyridazinyl |
| 107 | CH₂ | 4-pyridazinyl |
| 108 | CH₂ | 2-(2H-1,3-oxazinyl) |
| 109 | CH₂ | 2-(6H-1,3-oxazinyl) |
| 110 | CH₂ | 4-(6H-1,3-oxazinyl) |
| 111 | CH₂ | 6-(6H-1,3-oxazinyl) |
| 112 | CH₂ | [1,3,5]-2-triazinyl |
| 113 | CH₂ | [1,2,4]-3-triazinyl |
| 114 | CH₂ | [1,2,4]-5-triazinyl |
| 115 | CH₂ | [1,2,4]-6-triazinyl |
| 116 | CHCH₃ | oxiranyl |
| 117 | CHCH₃ | 3-methyl-2-oxiranyl |
| 118 | CHCH₃ | 2-oxetanyl |
| 119 | CHCH₃ | 3-hydroxy-3-methyl-2-oxetanyl |
| 120 | CHCH₃ | 3-hydroxy-3-ethyl-2-oxetanyl |
| 121 | CHCH₃ | 3-hydroxy-3-propyl-2-oxetanyl |
| 122 | CHCH₃ | 3-hydroxy-3-butyl-2-oxetanyl |
| 123 | CHCH₃ | 3-methoxy-3-methyl-2-oxetanyl |
| 124 | CHCH₃ | 3-methoxy-3-ethyl-2-oxetanyl |
| 125 | CHCH₃ | 3-methoxy-3-propyl-2-oxetanyl |
| 126 | CHCH₃ | 3-methoxy-3-butyl-2-oxetanyl |
| 127 | CHCH₃ | 3-trimethylsilyloxy-3-methyl-2-oxetanyl |
| 128 | CHCH₃ | 3-trimethylsilyloxy-3-ethyl-2-oxetanyl |
| 129 | CHCH₃ | 3-trimethylsilyloxy-3-propyl-2-oxetanyl |
| 130 | CHCH₃ | 3-trimethylsilyloxy-3-butyl-2-oxetanyl |
| 131 | CHCH₃ | 3-oxetanyl |
| 132 | CHCH₃ | 2-furyl |
| 133 | CHCH₃ | 4,5-dihydro-2-furyl |
| 134 | CHCH₃ | 2,3-dihydro-2-furyl |
| 135 | CHCH₃ | 3-furyl |
| 136 | CHCH₃ | 4,5-dihydro-3-furyl |
| 137 | CHCH₃ | 2,3-dihydro-3-furyl |
| 138 | CHCH₃ | 2-thienyl |
| 139 | CHCH₃ | 4,5-dihydro-2-thienyl |
| 140 | CHCH₃ | 2,3-dihydro-2-thienyl |
| 141 | CHCH₃ | 5-chloro-2-thienyl |
| 142 | CHCH₃ | 5-methyl-2-thienyl |
| 143 | CHCH₃ | 3-thienyl |
| 144 | CHCH₃ | 4,5-dihydro-3-thienyl |
| 145 | CHCH₃ | 2,3-dihydro-3-thienyl |
| 146 | CHCH₃ | 2-pyrrolyl |
| 147 | CHCH₃ | 2,5-dihydro-2-pyrrolyl |
| 148 | CHCH₃ | 3-pyrrole |
| 149 | CHCH₃ | 2,5-dihydro-3-pyrrolyl |
| 150 | CHCH₃ | 3-isoxazolyl |
| 151 | CHCH₃ | 4-methyl-3-isoxazolyl |
| 152 | CHCH₃ | 5-methyl-3-isoxazolyl |
| 153 | CHCH₃ | 4,5-dimethyl-3-isoxazolyl |
| 154 | CHCH₃ | 4,5-dihydro-3-isoxazolyl |
| 155 | CHCH₃ | 4-methyl-4,5-dihydro-3-isoxazolyl |
| 156 | CHCH₃ | 5-methyl-4,5-dihydro-3-isoxazolyl |
| 157 | CHCH₃ | 4,5-dimethyl-4,5-dihydro-3-isoxazolyl |
| 158 | CHCH₃ | 4-isoxazolyl |
| 159 | CHCH₃ | 3-methyl-4-isoxazolyl |
| 160 | CHCH₃ | 5-methyl-4-isoxazolyl |
| 161 | CHCH₃ | 5-cyclopropyl-4-isoxazolyl |
| 162 | CHCH₃ | 5-phenyl-4-isoxazolyl |
| 163 | CHCH₃ | 3,5-dimethyl-4-isoxazolyl |
| 164 | CHCH₃ | 4,5-dihydro-4-isoxazolyl |
| 165 | CHCH₃ | 3-methyl-4,5-dihydro-4-isoxazolyl |
| 166 | CHCH₃ | 5-methyl-4,5-dihydro-4-isoxazolyl |
| 167 | CHCH₃ | 3,5-dimethyl-4,5-dihydro-4-isoxazolyl |
| 168 | CHCH₃ | 5-isoxazolyl |
| 169 | CHCH₃ | 3-methyl-5-isoxazolyl |
| 170 | CHCH₃ | 4-methyl-5-isoxazolyl |
| 171 | CHCH₃ | 3,4-dimethyl-5-isoxazolyl |
| 172 | CHCH₃ | 4,5-dihydro-5-isoxazolyl |
| 173 | CHCH₃ | 3-methyl-4,5-dihydro-5-isoxazolyl |
| 174 | CHCH₃ | 4-methyl-4,5-dihydro-5-isoxazolyl |
| 175 | CHCH₃ | 3,4-dimethyl-4,5-dihydro-5-isoxazolyl |
| 176 | CHCH₃ | 3-isothiazolyl |
| 177 | CHCH₃ | 4-methyl-3-isothiazolyl |
| 178 | CHCH₃ | 5-methyl-3-isothiazolyl |
| 179 | CHCH₃ | 4-isothiazolyl |
| 180 | CHCH₃ | 3-methyl-4-isothiazolyl |
| 181 | CHCH₃ | 5-methyl-4-isothiazolyl |
| 182 | CHCH₃ | 5-isothiazolyl |
| 183 | CHCH₃ | 3-methyl-5-isothiazolyl |
| 184 | CHCH₃ | 4-methyl-5-isothiazolyl |
| 185 | CHCH₃ | 2-oxazolyl |
| 186 | CHCH₃ | 4-oxazolyl |
| 187 | CHCH₃ | 5-oxazolyl |
| 188 | CHCH₃ | 2-thiazolyl |
| 189 | CHCH₃ | 4-thiazolyl |
| 190 | CHCH₃ | 5-thiazolyl |
| 191 | CHCH₃ | 3-pyrazolyl |
| 192 | CHCH₃ | 4-pyrazolyl |
| 193 | CHCH₃ | 1-methyl-3-pyrazolyl |
| 194 | CHCH₃ | 1-methyl-4-pyrazolyl |
| 195 | CHCH₃ | 1-methyl-5-pyrazolyl |
| 196 | CHCH₃ | 2-imidazolyl |
| 197 | CHCH₃ | 1-methyl-2-imidazolyl |
| 198 | CHCH₃ | 5-methyl-[1,3,4]-2-oxadiazolyl |
| 199 | CHCH₃ | 5-methyl-[1,2,4]-3-oxadiazolyl |
| 200 | CHCH₃ | 5-methyl-[1,3,4]-2-thiadiazolyl |
| 201 | CHCH₃ | 5-methyl-[1,2,4]-3-thiadiazolyl |
| 202 | CHCH₃ | [1,2,4]-3-triazolyl |
| 203 | CHCH₃ | [1,2,3]-4-triazolyl |
| 204 | CHCH₃ | 2-pyridyl |
| 205 | CHCH₃ | 6-chloro-2-pyridyl |
| 206 | CHCH₃ | 6-methoxy-2-pyridyl |
| 207 | CHCH₃ | 6-trifluoromethyl-2-pyridyl |
| 208 | CHCH₃ | 3-pyridyl |
| 209 | CHCH₃ | 2-chloro-3-pyridyl |
| 210 | CHCH₃ | 2-methoxy-3-pyridyl |
| 211 | CHCH₃ | 4-pyridyl |
| 212 | CHCH₃ | 2-chloro-4-pyridyl |
| 213 | CHCH₃ | 2-methoxy-4-pyridyl |
| 214 | CHCH₃ | 2-ethoxy-4-pyridyl |
| 215 | CHCH₃ | 2-methylthio-4-pyridyl |
| 216 | CHCH₃ | 2-trifluoromethyl-5-pyridyl |
| 217 | CHCH₃ | 2-pyrimidinyl |
| 218 | CHCH₃ | 3-pyrimidinyl |
| 219 | CHCH₃ | 4-pyrimidinyl |
| 220 | CHCH₃ | 2-pyrazinyl |
| 221 | CHCH₃ | 3-pyridazinyl |
| 222 | CHCH₃ | 4-pyridazinyl |
| 223 | CHCH₃ | 2-(2H-1,3-oxazinyl) |
| 224 | CHCH₃ | 2-(6H-1,3-oxazinyl) |
| 225 | CHCH₃ | 4-(6H-1,3-oxazinyl) |
| 226 | CHCH₃ | 6-(6H-1,3-oxazinyl) |
| 227 | CHCH₃ | [1,3,5]-2-triazinyl |
| 228 | CHCH₃ | [1,2,4]-3-triazinyl |
| 229 | CHCH₃ | [1,2,4]-5-triazinyl |
| 230 | CHCH₃ | [1,2,4]-6-triazinyl |
| 231 | CHOH | oxiranyl |

TABLE A-continued

| No. | X¹ | Het |
|---|---|---|
| 232 | CHOH | 3-methyl-2-oxiranyl |
| 233 | CHOH | 2-oxetanyl |
| 234 | CHOH | 3-hydroxy-3-methyl-2-oxetanyl |
| 235 | CHOH | 3-hydroxy-3-ethyl-2-oxetanyl |
| 236 | CHOH | 3-hydroxy-3-propyl-2-oxetanyl |
| 237 | CHOH | 3-hydroxy-3-butyl-2-oxetanyl |
| 238 | CHOH | 3-methoxy-3-methyl-2-oxetanyl |
| 239 | CHOH | 3-methoxy-3-ethyl-2-oxetanyl |
| 240 | CHOH | 3-methoxy-3-propyl-2-oxetanyl |
| 241 | CHOH | 3-methoxy-3-butyl-2-oxetanyl |
| 242 | CHOH | 3-trimethylsilyloxy-3-methyl-2-oxetanyl |
| 243 | CHOH | 3-trimethylsilyloxy-3-ethyl-2-oxetanyl |
| 244 | CHOH | 3-trimethylsilyloxy-3-propyl-2-oxetanyl |
| 245 | CHOH | 3-trimethylsilyloxy-3-butyl-2-oxetanyl |
| 246 | CHOH | 3-oxetanyl |
| 247 | CHOH | 2-furyl |
| 248 | CHOH | 4,5-dihydro-2-furyl |
| 249 | CHOH | 2,3-dihydro-2-furyl |
| 250 | CHOH | 3-furyl |
| 251 | CHOH | 4,5-dihydro-3-furyl |
| 252 | CHOH | 2,3-dihydro-3-furyl |
| 253 | CHOH | 2-thienyl |
| 254 | CHOH | 4,5-dihydro-2-thienyl |
| 255 | CHOH | 2,3-dihydro-2-thienyl |
| 256 | CHOH | 5-chloro-2-thienyl |
| 257 | CHOH | 5-methyl-2-thienyl |
| 258 | CHOH | 3-thienyl |
| 259 | CHOH | 4,5-dihydro-3-thienyl |
| 260 | CHOH | 2,3-dihydro-3-thienyl |
| 261 | CHOH | 2-pyrrolyl |
| 262 | CHOH | 2,5-dihydro-2-pyrrolyl |
| 263 | CHOH | 3-pyrrole |
| 264 | CHOH | 2,5-dihydro-3-pyrrolyl |
| 265 | CHOH | 3-isoxazolyl |
| 266 | CHOH | 4-methyl-3-isoxazolyl |
| 267 | CHOH | 5-methyl-3-isoxazolyl |
| 268 | CHOH | 4,5-dimethyl-3-isoxazolyl |
| 269 | CHOH | 4,5-dihydro-3-isoxazolyl |
| 270 | CHOH | 4-methyl-4,5-dihydro-3-isoxazolyl |
| 271 | CHOH | 5-methyl-4,5-dihydro-3-isoxazolyl |
| 272 | CHOH | 4,5-dimethyl-4,5-dihydro-3-isoxazolyl |
| 273 | CHOH | 4-isoxazolyl |
| 274 | CHOH | 3-methyl-4-isoxazolyl |
| 275 | CHOH | 5-methyl-4-isoxazolyl |
| 276 | CHOH | 5-cyclopropyl-4-isoxazolyl |
| 277 | CHOH | 5-phenyl-4-isoxazolyl |
| 278 | CHOH | 3,5-dimethyl-4-isoxazolyl |
| 279 | CHOH | 4,5-dihydro-4-isoxazolyl |
| 280 | CHOH | 3-methyl-4,5-dihydro-4-isoxazolyl |
| 281 | CHOH | 5-methyl-4,5-dihydro-4-isoxazolyl |
| 282 | CHOH | 3,5-dimethyl-4,5-dihydro-4-isoxazolyl |
| 283 | CHOH | 5-isoxazolyl |
| 284 | CHOH | 3-methyl-5-isoxazolyl |
| 285 | CHOH | 4-methyl-5-isoxazolyl |
| 286 | CHOH | 3,4-dimethyl-5-isoxazolyl |
| 287 | CHOH | 4,5-dihydro-5-isoxazolyl |
| 288 | CHOH | 3-methyl-4,5-dihydro-5-isoxazolyl |
| 289 | CHOH | 4-methyl-4,5-dihydro-5-isoxazolyl |
| 290 | CHOH | 3,4-dimethyl-4,5-dihydro-5-isoxazolyl |
| 291 | CHOH | 3-isothiazolyl |
| 292 | CHOH | 4-methyl-3-isothiazolyl |
| 293 | CHOH | 5-methyl-3-isothiazolyl |
| 294 | CHOH | 4-isothiazolyl |
| 295 | CHOH | 3-methyl-4-isothiazolyl |
| 296 | CHOH | 5-methyl-4-isothiazolyl |
| 297 | CHOH | 5-isothiazolyl |
| 298 | CHOH | 3-methyl-5-isothiazolyl |
| 299 | CHOH | 4-methyl-5-isothiazolyl |
| 300 | CHOH | 2-oxazolyl |
| 301 | CHOH | 4-oxazolyl |
| 302 | CHOH | 5-oxazolyl |
| 303 | CHOH | 2-thiazolyl |
| 304 | CHOH | 4-thiazolyl |
| 305 | CHOH | 5-thiazolyl |
| 306 | CHOH | 3-pyrazolyl |
| 307 | CHOH | 4-pyrazolyl |
| 308 | CHOH | 1-methyl-3-pyrazolyl |
| 309 | CHOH | 1-methyl-4-pyrazolyl |
| 310 | CHOH | 1-methyl-5-pyrazolyl |
| 311 | CHOH | 2-imidazolyl |
| 312 | CHOH | 1-methyl-2-imidazolyl |
| 313 | CHOH | 5-methyl-[1,3,4]-2-oxadiazolyl |
| 314 | CHOH | 5-methyl-[1,2,4]-3-oxadiazolyl |
| 315 | CHOH | 5-methyl-[1,3,4]-2-thiadiazolyl |
| 316 | CHOH | 5-methyl-[1,2,4]-3-thiadiazolyl |
| 317 | CHOH | [1,2,4]-3-triazolyl |
| 318 | CHOH | [1,2,3]-4-triazolyl |
| 319 | CHOH | 2-pyridyl |
| 320 | CHOH | 6-chloro-2-pyridyl |
| 321 | CHOH | 6-methoxy-2-pyridyl |
| 322 | CHOH | 6-trifluoromethyl-2-pyridyl |
| 323 | CHOH | 3-pyridyl |
| 324 | CHOH | 2-chloro-3-pyridyl |
| 325 | CHOH | 2-methoxy-3-pyridyl |
| 326 | CHOH | 4-pyridyl |
| 327 | CHOH | 2-chloro-4-pyridyl |
| 328 | CHOH | 2-methoxy-4-pyridyl |
| 329 | CHOH | 2-ethoxy-4-pyridyl |
| 330 | CHOH | 2-methylthio-4-pyridyl |
| 331 | CHOH | 2-trifluoromethyl-5-pyridyl |
| 332 | CHOH | 2-pyrimidinyl |
| 333 | CHOH | 3-pyrimidinyl |
| 334 | CHOH | 4-pyrimidinyl |
| 335 | CHOH | 2-pyrazinyl |
| 336 | CHOH | 3-pyridazinyl |
| 337 | CHOH | 4-pyridazinyl |
| 338 | CHOH | 2-(2H-1,3-oxazinyl) |
| 339 | CHOH | 2-(6H-1,3-oxazinyl) |
| 340 | CHOH | 4-(6H-1,3-oxazinyl) |
| 341 | CHOH | 6-(6H-1,3-oxazinyl) |
| 342 | CHOH | [1,3,5]-2-triazinyl |
| 343 | CHOH | [1,2,4]-3-triazinyl |
| 344 | CHOH | [1,2,4]-5-triazinyl |
| 345 | CHOH | [1,2,4]-6-triazinyl |
| 346 | CHOCH₃ | oxiranyl |
| 347 | CHOCH₃ | 3-methyl-2-oxiranyl |
| 348 | CHOCH₃ | 2-oxetanyl |
| 349 | CHOCH₃ | 3-hydroxy-3-methyl-2-oxetanyl |
| 350 | CHOCH₃ | 3-hydroxy-3-ethyl-2-oxetanyl |
| 351 | CHOCH₃ | 3-hydroxy-3-propyl-2-oxetanyl |
| 352 | CHOCH₃ | 3-hydroxy-3-butyl-2-oxetanyl |
| 353 | CHOCH₃ | 3-methoxy-3-methyl-2-oxetanyl |
| 354 | CHOCH₃ | 3-methoxy-3-ethyl-2-oxetanyl |
| 355 | CHOCH₃ | 3-methoxy-3-propyl-2-oxetanyl |
| 356 | CHOCH₃ | 3-methoxy-3-butyl-2-oxetanyl |
| 357 | CHOCH₃ | 3-trimethylsilyloxy-3-methyl-2-oxetanyl |
| 358 | CHOCH₃ | 3-trimethylsilyloxy-3-ethyl-2-oxetanyl |
| 359 | CHOCH₃ | 3-trimethylsilyloxy-3-propyl-2-oxetanyl |
| 360 | CHOCH₃ | 3-trimethylsilyloxy-3-butyl-2-oxetanyl |
| 361 | CHOCH₃ | 3-oxetanyl |
| 362 | CHOCH₃ | 2-furyl |
| 363 | CHOCH₃ | 4,5-dihydro-2-furyl |
| 364 | CHOCH₃ | 2,3-dihydro-2-furyl |
| 365 | CHOCH₃ | 3-furyl |
| 366 | CHOCH₃ | 4,5-dihydro-3-furyl |
| 367 | CHOCH₃ | 2,3-dihydro-3-furyl |
| 368 | CHOCH₃ | 2-thienyl |
| 369 | CHOCH₃ | 4,5-dihydro-2-thienyl |
| 370 | CHOCH₃ | 2,3-dihydro-2-thienyl |
| 371 | CHOCH₃ | 5-chloro-2-thienyl |
| 372 | CHOCH₃ | 5-methyl-2-thienyl |
| 373 | CHOCH₃ | 3-thienyl |
| 374 | CHOCH₃ | 4,5-dihydro-3-thienyl |
| 375 | CHOCH₃ | 2,3-dihydro-3-thienyl |
| 376 | CHOCH₃ | 2-pyrrolyl |
| 377 | CHOCH₃ | 2,5-dihydro-2-pyrrolyl |
| 378 | CHOCH₃ | 3-pyrrole |
| 379 | CHOCH₃ | 2,5-dihydro-3-pyrrolyl |
| 380 | CHOCH₃ | 3-isoxazolyl |
| 381 | CHOCH₃ | 4-methyl-3-isoxazolyl |
| 382 | CHOCH₃ | 5-methyl-3-isoxazolyl |
| 383 | CHOCH₃ | 4,5-dimethyl-3-isoxazolyl |
| 384 | CHOCH₃ | 4,5-dihydro-3-isoxazolyl |
| 385 | CHOCH₃ | 4-methyl-4,5-dihydro-3-isoxazolyl |

TABLE A-continued

| No. | X¹ | Het |
|---|---|---|
| 386 | CHOCH₃ | 5-methyl-4,5-dihydro-3-isoxazolyl |
| 387 | CHOCH₃ | 4,5-dimethyl-4,5-dihydro-3-isoxazolyl |
| 388 | CHOCH₃ | 4-isoxazolyl |
| 389 | CHOCH₃ | 3-methyl-4-isoxazolyl |
| 390 | CHOCH₃ | 5-methyl-4-isoxazolyl |
| 391 | CHOCH₃ | 5-cyclopropyl-4-isoxazolyl |
| 392 | CHOCH₃ | 5-phenyl-4-isoxazolyl |
| 393 | CHOCH₃ | 3,5-dimethyl-4-isoxazolyl |
| 394 | CHOCH₃ | 4,5-dihydro-4-isoxazolyl |
| 395 | CHOCH₃ | 3-methyl-4,5-dihydro-4-isoxazolyl |
| 396 | CHOCH₃ | 5-methyl-4,5-dihydro-4-isoxazolyl |
| 397 | CHOCH₃ | 3,5-dimethyl-4,5-dihydro-4-isoxazolyl |
| 398 | CHOCH₃ | 5-isoxazolyl |
| 399 | CHOCH₃ | 3-methyl-5-isoxazolyl |
| 400 | CHOCH₃ | 4-methyl-5-isoxazolyl |
| 401 | CHOCH₃ | 3,4-dimethyl-5-isoxazolyl |
| 402 | CHOCH₃ | 4,5-dihydro-5-isoxazolyl |
| 403 | CHOCH₃ | 3-methyl-4,5-dihydro-5-isoxazolyl |
| 404 | CHOCH₃ | 4-methyl-4,5-dihydro-5-isoxazolyl |
| 405 | CHOCH₃ | 3,4-dimethyl-4,5-dihydro-5-isoxazolyl |
| 406 | CHOCH₃ | 3-isothiazolyl |
| 407 | CHOCH₃ | 4-methyl-3-isothiazolyl |
| 408 | CHOCH₃ | 5-methyl-3-isothiazolyl |
| 409 | CHOCH₃ | 4-isothiazolyl |
| 410 | CHOCH₃ | 3-methyl-4-isothiazolyl |
| 411 | CHOCH₃ | 5-methyl-4-isothiazotyl |
| 412 | CHOCH₃ | 5-isothiazolyl |
| 413 | CHOCH₃ | 3-methyl-5-isothiazolyl |
| 414 | CHOCH₃ | 4-methyl-5-isothiazolyl |
| 415 | CHOCH₃ | 2-oxazolyl |
| 416 | CHOCH₃ | 4-oxazolyl |
| 417 | CHOCH₃ | 5-oxazolyl |
| 418 | CHOCH₃ | 2-thiazolyl |
| 419 | CHOCH₃ | 4-thiazolyl |
| 420 | CHOCH₃ | 5-thiazolyl |
| 421 | CHOCH₃ | 3-pyrazolyl |
| 422 | CHOCH₃ | 4-pyrazolyl |
| 423 | CHOCH₃ | 1-methyl-3-pyrazolyl |
| 424 | CHOCH₃ | 1-methyl-4-pyrazolyl |
| 425 | CHOCH₃ | 1-methyl-5-pyrazolyl |
| 426 | CHOCH₃ | 2-imidazolyl |
| 427 | CHOCH₃ | 1-methyl-2-imidazolyl |
| 428 | CHOCH₃ | 5-methyl-[1,3,4]-2-oxadiazolyl |
| 429 | CHOCH₃ | 5-methyl-[1,2,4]-3-oxadiazolyl |
| 430 | CHOCH₃ | 5-methyl-[1,3,4]-2-thiadiazolyl |
| 431 | CHOCH₃ | 5-methyl-[1,2,4]-3-thiadiazolyl |
| 432 | CHOCH₃ | [1,2,4]-3-triazolyl |
| 433 | CHOCH₃ | [1,2,3]-4-triazolyl |
| 434 | CHOCH₃ | 2-pyridyl |
| 435 | CHOCH₃ | 6-chloro-2-pyridyl |
| 436 | CHOCH₃ | 6-methoxy-2-pyridyl |
| 437 | CHOCH₃ | 6-trifluoromethyl-2-pyridyl |
| 438 | CHOCH₃ | 3-pyridyl |
| 439 | CHOCH₃ | 2-chloro-3-pyridyl |
| 440 | CHOCH₃ | 2-methoxy-3-pyridyl |
| 441 | CHOCH₃ | 4-pyridyl |
| 442 | CHOCH₃ | 2-chloro-4-pyridyl |
| 443 | CHOCH₃ | 2-methoxy-4-pyridyl |
| 444 | CHOCH₃ | 2-ethoxy-4-pyridyl |
| 445 | CHOCH₃ | 2-methylthio-4-pyridyl |
| 446 | CHOCH₃ | 2-trifluoromethyl-5-pyridyl |
| 447 | CHOCH₃ | 2-pyrimidinyl |
| 448 | CHOCH₃ | 3-pyrimidinyl |
| 449 | CHOCH₃ | 4-pyrimidinyl |
| 450 | CHOCH₃ | 2-pyrazinyl |
| 451 | CHOCH₃ | 3-pyridazinyl |
| 452 | CHOCH₃ | 4-pyridazinyl |
| 453 | CHOCH₃ | 2-(2H-1,3-oxazinyl) |
| 454 | CHOCH₃ | 2-(6H-1,3-oxazinyl) |
| 455 | CHOCH₃ | 4-(6H-1,3-oxazinyl) |
| 456 | CHOCH₃ | 6-(6H-1,3-oxazinyl) |
| 457 | CHOCH₃ | [1,3,5]-2-triazinyl |
| 458 | CHOCH₃ | [1,2,4]-3-triazinyl |
| 459 | CHOCH₃ | [1,2,4]-5-triazinyl |
| 460 | CHOCH₃ | [1,2,4]-6-triazinyl |
| 461 | CHOCOCH₃ | oxiranyl |
| 462 | CHOCOCH₃ | 3-methyl-2-oxiranyl |
| 463 | CHOCOCH₃ | 2-oxetanyl |
| 464 | CHOCOCH₃ | 3-hydroxy-3-methyl-2-oxetanyl |
| 465 | CHOCOCH₃ | 3-hydroxy-3-ethyl-2-oxetanyl |
| 466 | CHOCOCH₃ | 3-hydroxy-3-propyl-2-oxetanyl |
| 467 | CHOCOCH₃ | 3-hydroxy-3-butyl-2-oxetanyl |
| 468 | CHOCOCH₃ | 3-methoxy-3-methyl-2-oxetanyl |
| 469 | CHOCOCH₃ | 3-methoxy-3-ethyl-2-oxetanyl |
| 470 | CHOCOCH₃ | 3-methoxy-3-propyl-2-oxetanyl |
| 471 | CHOCOCH₃ | 3-methoxy-3-butyl-2-oxetanyl |
| 472 | CHOCOCH₃ | 3-trimethylsilyloxy-3-methyl-2-oxetanyl |
| 473 | CHOCOCH₃ | 3-trimethylsilyloxy-3-ethyl-2-oxetanyl |
| 474 | CHOCOCH₃ | 3-trimethylsilyloxy-3-propyl-2-oxetanyl |
| 475 | CHOCOCH₃ | 3-trimethylsilyloxy-3-butyl-2-oxetanyl |
| 476 | CHOCOCH₃ | 3-oxetanyl |
| 477 | CHOCOCH₃ | 2-furyl |
| 478 | CHOCOCH₃ | 4,5-dihydro-2-furyl |
| 479 | CHOCOCH₃ | 2,3-dihydro-2-furyl |
| 480 | CHOCOCH₃ | 3-furyl |
| 481 | CHOCOCH₃ | 4,5-dihydro-3-furyl |
| 482 | CHOCOCH₃ | 2,3-dihydro-3-furyl |
| 483 | CHOCOCH₃ | 2-thienyl |
| 484 | CHOCOCH₃ | 4,5-dihydro-2-thienyl |
| 485 | CHOCOCH₃ | 2,3-dihydro-2-thienyl |
| 486 | CHOCOCH₃ | 5-chloro-2-thienyl |
| 487 | CHOCOCH₃ | 5-methyl-2-thienyl |
| 488 | CHOCOCH₃ | 3-thienyl |
| 489 | CHOCOCH₃ | 4,5-dihydro-3-thienyl |
| 490 | CHOCOCH₃ | 2,3-dihydro-3-thienyl |
| 491 | CHOCOCH₃ | 2-pyrrolyl |
| 492 | CHOCOCH₃ | 2,5-dihydro-2-pyrrolyl |
| 493 | CHOCOCH₃ | 3-pyrrole |
| 494 | CHOCOCH₃ | 2,5-dihydro-3-pyrrolyl |
| 495 | CHOCOCH₃ | 3-isoxazolyl |
| 496 | CHOCOCH₃ | 4-methyl-3-isoxazolyl |
| 497 | CHOCOCH₃ | 5-methyl-3-isoxazolyl |
| 498 | CHOCOCH₃ | 4,5-dimethyl-3-isoxazolyl |
| 499 | CHOCOCH₃ | 4,5-dihydro-3-isoxazolyl |
| 500 | CHOCOCH₃ | 4-methyl-4,5-dihydro-3-isoxazolyl |
| 501 | CHOCOCH₃ | 5-methyl-4,5-dihydro-3-isoxazolyl |
| 502 | CHOCOCH₃ | 4,5-dimethyl-4,5-dihydro-3-isoxazolyl |
| 503 | CHOCOCH₃ | 4-isoxazolyl |
| 504 | CHOCOCH₃ | 3-methyl-4-isoxazolyl |
| 505 | CHOCOCH₃ | 5-methyl-4-isoxazolyl |
| 506 | CHOCOCH₃ | 5-cyclopropyl-4-isoxazolyl |
| 507 | CHOCOCH₃ | 5-phenyl-4-isoxazolyl |
| 508 | CHOCOCH₃ | 3,5-dimethyl-4-isoxazolyl |
| 509 | CHOCOCH₃ | 4,5-dihydro-4-isoxazolyl |
| 510 | CHOCOCH₃ | 3-methyl-4,5-dihydro-4-isoxazolyl |
| 511 | CHOCOCH₃ | 5-methyl-4,5-dihydro-4-isoxazolyl |
| 512 | CHOCOCH₃ | 3,5-dimethyl-4,5-dihydro-4-isoxazolyl |
| 513 | CHOCOCH₃ | 5-isoxazolyl |
| 514 | CHOCOCH₃ | 3-methyl-5-isoxazolyl |
| 515 | CHOCOCH₃ | 4-methyl-5-isoxazolyl |
| 516 | CHOCOCH₃ | 3,4-dimethyl-5-isoxazolyl |
| 517 | CHOCOCH₃ | 4,5-dihydro-5-isoxazolyl |
| 518 | CHOCOCH₃ | 3-methyl-4,5-dihydro-5-isoxazolyl |
| 519 | CHOCOCH₃ | 4-methyl-4,5-dihydro-5-isoxazolyl |
| 520 | CHOCOCH₃ | 3,4-dimethyl-4,5-dihydro-5-isoxazolyl |
| 521 | CHOCOCH₃ | 3-isothiazolyl |
| 522 | CHOCOCH₃ | 4-methyl-3-isothiazolyl |
| 523 | CHOCOCH₃ | 5-methyl-3-isothiazolyl |
| 524 | CHOCOCH₃ | 4-isothiazolyl |
| 525 | CHOCOCH₃ | 3-methyl-4-isothiazolyl |
| 526 | CHOCOCH₃ | 5-methyl-4-isothiazolyl |
| 527 | CHOCOCH₃ | 5-isothiazolyl |
| 528 | CHOCOCH₃ | 3-methyl-5-isothiazolyl |
| 529 | CHOCOCH₃ | 4-methyl-5-isothiazolyl |
| 530 | CHOCOCH₃ | 2-oxazolyl |
| 531 | CHOCOCH₃ | 4-oxazolyl |
| 532 | CHOCOCH₃ | 5-oxazolyl |
| 533 | CHOCOCH₃ | 2-thiazolyl |
| 534 | CHOCOCH₃ | 4-thiazolyl |
| 535 | CHOCOCH₃ | 5-thiazolyl |
| 536 | CHOCOCH₃ | 3-pyrazolyl |
| 537 | CHOCOCH₃ | 4-pyrazolyl |
| 538 | CHOCOCH₃ | 1-methyl-3-pyrazolyl |
| 539 | CHOCOCH₃ | 1-methyl-4-pyrazolyl |

TABLE A-continued

| No. | X¹ | Het |
|---|---|---|
| 540 | CHOCOCH₃ | 1-methyl-5-pyrazolyl |
| 541 | CHOCOCH₃ | 2-imidazolyl |
| 542 | CHOCOCH₃ | 1-methyl-2-imidazolyl |
| 543 | CHOCOCH₃ | 5-methyl-[1,3,4]-2-oxadiazolyl |
| 544 | CHOCOCH₃ | 5-methyl-[1,2,4]-3-oxadiazolyl |
| 545 | CHOCOCH₃ | 5-methyl-[1,3,4]-2-thiadiazolyl |
| 546 | CHOCOCH₃ | 5-methyl-[1,2,4]-3-thiadiazolyl |
| 547 | CHOCOCH₃ | [1,2,4]-3-triazolyl |
| 548 | CHOCOCH₃ | [1,2,3]-4-triazolyl |
| 549 | CHOCOCH₃ | 2-pyridyl |
| 550 | CHOCOCH₃ | 6-chloro-2-pyridyl |
| 551 | CHOCOCH₃ | 6-methoxy-2-pyridyl |
| 552 | CHOCOCH₃ | 6-trifluoromethyl-2-pyridyl |
| 553 | CHOCOCH₃ | 3-pyridyl |
| 554 | CHOCOCH₃ | 2-chloro-3-pyridyl |
| 555 | CHOCOCH₃ | 2-methoxy-3-pyridyl |
| 556 | CHOCOCH₃ | 4-pyridyl |
| 557 | CHOCOCH₃ | 2-chloro-4-pyridyl |
| 558 | CHOCOCH₃ | 2-methoxy-4-pyridyl |
| 559 | CHOCOCH₃ | 2-ethoxy-4-pyridyl |
| 560 | CHOCOCH₃ | 2-methylthio-4-pyridyl |
| 561 | CHOCOCH₃ | 2-trifluoromethyl-5-pyridyl |
| 562 | CHOCOCH₃ | 2-pyrimidinyl |
| 563 | CHOCOCH₃ | 3-pyrimidinyl |
| 564 | CHOCOCH₃ | 4-pyrimidinyl |
| 565 | CHOCOCH₃ | 2-pyrazinyl |
| 566 | CHOCOCH₃ | 3-pyridazinyl |
| 567 | CHOCOCH₃ | 4-pyridazinyl |
| 568 | CHOCOCH₃ | 2-(2H-1,3-oxazinyl) |
| 569 | CHOCOCH₃ | 2-(6H-1,3-oxazinyl) |
| 570 | CHOCOCH₃ | 4-(6H-1,3-oxazinyl) |
| 571 | CHOCOCH₃ | 6-(6H-1,3-oxazinyl) |
| 572 | CHOCOCH₃ | [1,3,5]-2-triazinyl |
| 573 | CHOCOCH₃ | [1,2,4]-3-triazinyl |
| 574 | CHOCOCH₃ | [1,2,4]-5-triazinyl |
| 575 | CHOCOCH₃ | [1,2,4]-6-triazinyl |
| 576 | CHOSO₂CH₃ | oxiranyl |
| 577 | CHOSO₂CH₃ | 3-methyl-2-oxiranyl |
| 578 | CHOSO₂CH₃ | 2-oxetanyl |
| 579 | CHOSO₂CH₃ | 3-hydroxy-3-methyl-2-oxetanyl |
| 580 | CHOSO₂CH₃ | 3-hydroxy-3-ethyl-2-oxetanyl |
| 581 | CHOSO₂CH₃ | 3-hydroxy-3-propyl-2-oxetanyl |
| 582 | CHOSO₂CH₃ | 3-hydroxy-3-butyl-2-oxetanyl |
| 583 | CHOSO₂CH₃ | 3-methoxy-3-methyl-2-oxetanyl |
| 584 | CHOSO₂CH₃ | 3-methoxy-3-ethyl-2-oxetanyl |
| 585 | CHOSO₂CH₃ | 3-methoxy-3-propyl-2-oxetanyl |
| 586 | CHOSO₂CH₃ | 3-methoxy-3-butyl-2-oxetanyl |
| 587 | CHOSO₂CH₃ | 3-trimethylsilyloxy-3-methyl-2-oxetanyl |
| 588 | CHOSO₂CH₃ | 3-trimethylsilyloxy-3-ethyl-2-oxetanyl |
| 589 | CHOSO₂CH₃ | 3-trimethylsilyloxy-3-propyl-2-oxetanyl |
| 590 | CHOSO₂CH₃ | 3-trimethylsilyloxy-3-butyl-2-oxetanyl |
| 591 | CHOSO₂CH₃ | 3-oxetanyl |
| 592 | CHOSO₂CH₃ | 2-furyl |
| 593 | CHOSO₂CH₃ | 4,5-dihydro-2-furyl |
| 594 | CHOSO₂CH₃ | 2,3-dihydro-2-furyl |
| 595 | CHOSO₂CH₃ | 3-furyl |
| 596 | CHOSO₂CH₃ | 4,5-dihydro-3-furyl |
| 597 | CHOSO₂CH₃ | 2,3-dihydro-3-furyl |
| 598 | CHOSO₂CH₃ | 2-thienyl |
| 599 | CHOSO₂CH₃ | 4,5-dihydro-2-thienyl |
| 600 | CHOSO₂CH₃ | 2,3-dihydro-2-thienyl |
| 601 | CHOSO₂CH₃ | 5-chloro-2-thienyl |
| 602 | CHOSO₂CH₃ | 5-methyl-2-thienyl |
| 603 | CHOSO₂CH₃ | 3-thienyl |
| 604 | CHOSO₂CH₃ | 4,5-dihydro-3-thienyl |
| 605 | CHOSO₂CH₃ | 2,3-dihydro-3-thienyl |
| 606 | CHOSO₂CH₃ | 2-pyrrolyl |
| 607 | CHOSO₂CH₃ | 2,5-dihydro-2-pyrrolyl |
| 608 | CHOSO₂CH₃ | 3-pyrrole |
| 609 | CHOSO₂CH₃ | 2,5-dihydro-3-pyrrolyl |
| 610 | CHOSO₂CH₃ | 3-isoxazolyl |
| 611 | CHOSO₂CH₃ | 4-methyl-3-isoxazolyl |
| 612 | CHOSO₂CH₃ | 5-methyl-3-isoxazolyl |
| 613 | CHOSO₂CH₃ | 4,5-dimethyl-3-isoxazolyl |
| 614 | CHOSO₂CH₃ | 4,5-dihydro-3-isoxazolyl |
| 615 | CHOSO₂CH₃ | 4-methyl-4,5-dihydro-3-isoxazolyl |
| 616 | CHOSO₂CH₃ | 5-methyl-4,5-dihydro-3-isoxazolyl |
| 617 | CHOSO₂CH₃ | 4,5-dimethyl-4,5-dihydro-3-isoxazolyl |
| 618 | CHOSO₂CH₃ | 4-isoxazolyl |
| 619 | CHOSO₂CH₃ | 3-methyl-4-isoxazolyl |
| 620 | CHOSO₂CH₃ | 5-methyl-4-isoxazolyl |
| 621 | CHOSO₂CH₃ | 5-cyclopropyl-4-isoxazolyl |
| 622 | CHOSO₂CH₃ | 5-phenyl-4-isoxazolyl |
| 623 | CHOSO₂CH₃ | 3,5-dimethyl-4-isoxazolyl |
| 624 | CHOSO₂CH₃ | 4,5-dihydro-4-isoxazolyl |
| 625 | CHOSO₂CH₃ | 3-methyl-4,5-dihydro-4-isoxazolyl |
| 626 | CHOSO₂CH₃ | 5-methyl-4,5-dihydro-4-isoxazolyl |
| 627 | CHOSO₂CH₃ | 3,5-dimethyl-4,5-dihydro-4-isoxazolyl |
| 628 | CHOSO₂CH₃ | 5-isoxazolyl |
| 629 | CHOSO₂CH₃ | 3-methyl-5-isoxazolyl |
| 630 | CHOSO₂CH₃ | 4-methyl-5-isoxazolyl |
| 631 | CHOSO₂CH₃ | 3,4-dimethyl-5-isoxazolyl |
| 632 | CHOSO₂CH₃ | 4,5-dihydro-5-isoxazolyl |
| 633 | CHOSO₂CH₃ | 3-methyl-4,5-dihydro-5-isoxazolyl |
| 634 | CHOSO₂CH₃ | 4-methyl-4,5-dihydro-5-isoxazolyl |
| 635 | CHOSO₂CH₃ | 3,4-dimethyl-4,5-dihydro-5-isoxazolyl |
| 636 | CHOSO₂CH₃ | 3-isothiazolyl |
| 637 | CHOSO₂CH₃ | 4-methyl-3-isothiazolyl |
| 638 | CHOSO₂CH₃ | 5-methyl-3-isothiazolyl |
| 639 | CHOSO₂CH₃ | 4-isothiazolyl |
| 640 | CHOSO₂CH₃ | 3-methyl-4-isothiazolyl |
| 641 | CHOSO₂CH₃ | 5-methyl-4-isothiazolyl |
| 642 | CHOSO₂CH₃ | 5-isothiazolyl |
| 643 | CHOSO₂CH₃ | 3-methyl-5-isothiazolyl |
| 644 | CHOSO₂CH₃ | 4-methyl-5-isothiazolyl |
| 645 | CHOSO₂CH₃ | 2-oxazolyl |
| 646 | CHOSO₂CH₃ | 4-oxazolyl |
| 647 | CHOSO₂CH₃ | 5-oxazolyl |
| 648 | CHOSO₂CH₃ | 2-thiazolyl |
| 649 | CHOSO₂CH₃ | 4-thiazolyl |
| 650 | CHOSO₂CH₃ | 5-thiazolyl |
| 651 | CHOSO₂CH₃ | 3-pyrazolyl |
| 652 | CHOSO₂CH₃ | 4-pyrazolyl |
| 653 | CHOSO₂CH₃ | 1-methyl-3-pyrazolyl |
| 654 | CHOSO₂CH₃ | 1-methyl-4-pyrazolyl |
| 655 | CHOSO₂CH₃ | 1-methyl-5-pyrazolyl |
| 656 | CHOSO₂CH₃ | 2-imidazolyl |
| 657 | CHOSO₂CH₃ | 1-methyl-2-imidazolyl |
| 658 | CHOSO₂CH₃ | 5-methyl-[1,3,4]-2-oxadiazolyl |
| 659 | CHOSO₂CH₃ | 5-methyl-[1,2,4]-3-oxadiazolyl |
| 660 | CHOSO₂CH₃ | 5-methyl-[1,3,4]-2-thiadiazolyl |
| 661 | CHOSO₂CH₃ | 5-methyl-[1,2,4]-3-thiadiazolyl |
| 662 | CHOSO₂CH₃ | [1,2,4]-3-triazolyl |
| 663 | CHOSO₂CH₃ | [1,2,3]-4-triazolyl |
| 664 | CHOSO₂CH₃ | 2-pyridyl |
| 665 | CHOSO₂CH₃ | 6-chloro-2-pyridyl |
| 666 | CHOSO₂CH₃ | 6-methoxy-2-pyridyl |
| 667 | CHOSO₂CH₃ | 6-trifluoromethyl-2-pyridyl |
| 668 | CHOSO₂CH₃ | 3-pyridyl |
| 669 | CHOSO₂CH₃ | 2-chloro-3-pyridyl |
| 670 | CHOSO₂CH₃ | 2-methoxy-3-pyridyl |
| 671 | CHOSO₂CH₃ | 4-pyridyl |
| 672 | CHOSO₂CH₃ | 2-chloro-4-pyridyl |
| 673 | CHOSO₂CH₃ | 2-methoxy-4-pyridyl |
| 674 | CHOSO₂CH₃ | 2-ethoxy-4-pyridyl |
| 675 | CHOSO₂CH₃ | 2-methylthio-4-pyridyl |
| 676 | CHOSO₂CH₃ | 2-trifluoromethyl-5-pyridyl |
| 677 | CHOSO₂CH₃ | 2-pyrimidinyl |
| 678 | CHOSO₂CH₃ | 3-pyrimidinyl |
| 679 | CHOSO₂CH₃ | 4-pyrimidinyl |
| 680 | CHOSO₂CH₃ | 2-pyrazinyl |
| 681 | CHOSO₂CH₃ | 3-pyridazinyl |
| 682 | CHOSO₂CH₃ | 4-pyridazinyl |
| 683 | CHOSO₂CH₃ | 2-(2H-1,3-oxazinyl) |
| 684 | CHOSO₂CH₃ | 2-(6H-1,3-oxazinyl) |
| 685 | CHOSO₂CH₃ | 4-(6H-1,3-oxazinyl) |
| 686 | CHOSO₂CH₃ | 6-(6H-1,3-oxazinyl) |
| 687 | CHOSO₂CH₃ | [1,3,5]-2-triazinyl |
| 688 | CHOSO₂CH₃ | [1,2,4]-3-triazinyl |
| 689 | CHOSO₂CH₃ | [1,2,4]-5-triazinyl |
| 690 | CHOSO₂CH₃ | [1,2,4]-6-triazinyl |
| 691 | CH₂CH₂ | oxiranyl |
| 692 | CH₂CH₂ | 3-methyl-2-oxiranyl |
| 693 | CH₂CH₂ | 2-oxetanyl |

TABLE A-continued

| No. | X¹ | Het |
|---|---|---|
| 694 | CH₂CH₂ | 3-hydroxy-3-methyl-2-oxetanyl |
| 695 | CH₂CH₂ | 3-hydroxy-3-ethyl-2-oxetanyl |
| 696 | CH₂CH₂ | 3-hydroxy-3-propyl-2-oxetanyl |
| 697 | CH₂CH₂ | 3-hydroxy-3-butyl-2-oxetanyl |
| 698 | CH₂CH₂ | 3-methoxy-3-methyl-2-oxetanyl |
| 699 | CH₂CH₂ | 3-methoxy-3-ethyl-2-oxetanyl |
| 700 | CH₂CH₂ | 3-methoxy-3-propyl-2-oxetanyl |
| 701 | CH₂CH₂ | 3-methoxy-3-butyl-2-oxetanyl |
| 702 | CH₂CH₂ | 3-trimethylsilyloxy-3-methyl-2-oxetanyl |
| 703 | CH₂CH₂ | 3-trimethylsilyloxy-3-ethyl-2-oxetanyl |
| 704 | CH₂CH₂ | 3-trimethylsilyloxy-3-propyl-2-oxetanyl |
| 705 | CH₂CH₂ | 3-trimethylsilyloxy-3-butyl-2-oxetanyl |
| 706 | CH₂CH₂ | 3-oxetanyl |
| 707 | CH₂CH₂ | 2-furyl |
| 708 | CH₂CH₂ | 4,5-dihydro-2-furyl |
| 709 | CH₂CH₂ | 2,3-dihydro-2-furyl |
| 710 | CH₂CH₂ | 3-furyl |
| 711 | CH₂CH₂ | 4,5-dihydro-3-furyl |
| 712 | CH₂CH₂ | 2,3-dihydro-3-furyl |
| 713 | CH₂CH₂ | 2-thienyl |
| 714 | CH₂CH₂ | 4,5-dihydro-2-thienyl |
| 715 | CH₂CH₂ | 2,3-dihydro-2-thienyl |
| 716 | CH₂CH₂ | 5-chloro-2-thienyl |
| 717 | CH₂CH₂ | 5-methyl-2-thienyl |
| 718 | CH₂CH₂ | 3-thienyl |
| 719 | CH₂CH₂ | 4,5-dihydro-3-thienyl |
| 720 | CH₂CH₂ | 2,3-dihydro-3-thienyl |
| 721 | CH₂CH₂ | 2-pyrrolyl |
| 722 | CH₂CH₂ | 2,5-dihydro-2-pyrrolyl |
| 723 | CH₂CH₂ | 3-pyrrole |
| 724 | CH₂CH₂ | 2,5-dihydro-3-pyrrolyl |
| 725 | CH₂CH₂ | 3-isoxazolyl |
| 726 | CH₂CH₂ | 4-methyl-3-isoxazolyl |
| 727 | CH₂CH₂ | 5-methyl-3-isoxazolyl |
| 728 | CH₂CH₂ | 4,5-dimethyl-3-isoxazolyl |
| 729 | CH₂CH₂ | 4,5-dihydro-3-isoxazolyl |
| 730 | CH₂CH₂ | 4-methyl-4,5-dihydro-3-isoxazolyl |
| 731 | CH₂CH₂ | 5-methyl-4,5-dihydro-3-isoxazolyl |
| 732 | CH₂CH₂ | 4,5-dimethyl-4,5-dihydro-3-isoxazolyl |
| 733 | CH₂CH₂ | 4-isoxazolyl |
| 734 | CH₂CH₂ | 3-methyl-4-isoxazolyl |
| 735 | CH₂CH₂ | 5-methyl-4-isoxazolyl |
| 736 | CH₂CH₂ | 5-cyclopropyl-4-isoxazolyl |
| 737 | CH₂CH₂ | 5-phenyl-4-isoxazolyl |
| 738 | CH₂CH₂ | 3,5-dimethyl-4-isoxazolyl |
| 739 | CH₂CH₂ | 4,5-dihydro-4-isoxazolyl |
| 740 | CH₂CH₂ | 3-methyl-4,5-dihydro-4-isoxazolyl |
| 741 | CH₂CH₂ | 5-methyl-4,5-dihydro-4-isoxazolyl |
| 742 | CH₂CH₂ | 3,5-dimethyl-4,5-dihydro-4-isoxazolyl |
| 743 | CH₂CH₂ | 5-isoxazolyl |
| 744 | CH₂CH₂ | 3-methyl-5-isoxazolyl |
| 745 | CH₂CH₂ | 4-methyl-5-isoxazolyl |
| 746 | CH₂CH₂ | 3,4-dimethyl-5-isoxazolyl |
| 747 | CH₂CH₂ | 4,5-dihydro-5-isoxazolyl |
| 748 | CH₂CH₂ | 3-methyl-4,5-dihydro-5-isoxazolyl |
| 749 | CH₂CH₂ | 4-methyl-4,5-dihydro-5-isoxazolyl |
| 750 | CH₂CH₂ | 3,4-dimethyl-4,5-dihydro-5-isoxazolyl |
| 751 | CH₂CH₂ | 3-isothiazolyl |
| 752 | CH₂CH₂ | 4-methyl-3-isothiazolyl |
| 753 | CH₂CH₂ | 5-methyl-3-isothiazolyl |
| 754 | CH₂CH₂ | 4-isothiazolyl |
| 755 | CH₂CH₂ | 3-methyl-4-isothiazolyl |
| 756 | CH₂CH₂ | 5-methyl-4-isothiazolyl |
| 757 | CH₂CH₂ | 5-isothiazolyl |
| 758 | CH₂CH₂ | 3-methyl-5-isothiazolyl |
| 759 | CH₂CH₂ | 4-methyl-5-isothiazolyl |
| 760 | CH₂CH₂ | 2-oxazolyl |
| 761 | CH₂CH₂ | 4-oxazolyl |
| 762 | CH₂CH₂ | 5-oxazolyl |
| 763 | CH₂CH₂ | 2-thiazolyl |
| 764 | CH₂CH₂ | 4-thiazolyl |
| 765 | CH₂CH₂ | 5-thiazolyl |
| 766 | CH₂CH₂ | 3-pyrazolyl |
| 767 | CH₂CH₂ | 4-pyrazolyl |
| 768 | CH₂CH₂ | 1-methyl-3-pyrazolyl |
| 769 | CH₂CH₂ | 1-methyl-4-pyrazolyl |
| 770 | CH₂CH₂ | 1-methyl-5-pyrazolyl |
| 771 | CH₂CH₂ | 2-imidazolyl |
| 772 | CH₂CH₂ | 1-methyl-2-imidazolyl |
| 773 | CH₂CH₂ | 5-methyl-[1,3,4]-2-oxadiazolyl |
| 774 | CH₂CH₂ | 5-methyl-[1,2,4]-3-oxadiazolyl |
| 775 | CH₂CH₂ | 5-methyl-[1,3,4]-2-thiadiazolyl |
| 776 | CH₂CH₂ | 5-methyl-[1,2,4]-3-thiadiazolyl |
| 777 | CH₂CH₂ | [1,2,4]-3-triazolyl |
| 778 | CH₂CH₂ | [1,2,3]-4-triazolyl |
| 779 | CH₂CH₂ | 2-pyridyl |
| 780 | CH₂CH₂ | 6-chloro-2-pyridyl |
| 781 | CH₂CH₂ | 6-methoxy-2-pyridyl |
| 782 | CH₂CH₂ | 6-trifluoromethyl-2-pyridyl |
| 783 | CH₂CH₂ | 3-pyridyl |
| 784 | CH₂CH₂ | 2-chloro-3-pyridyl |
| 785 | CH₂CH₂ | 2-methoxy-3-pyridyl |
| 786 | CH₂CH₂ | 4-pyridyl |
| 787 | CH₂CH₂ | 2-chloro-4-pyridyl |
| 788 | CH₂CH₂ | 2-methoxy-4-pyridyl |
| 789 | CH₂CH₂ | 2-ethoxy-4-pyridyl |
| 790 | CH₂CH₂ | 2-methylthio-4-pyridyl |
| 791 | CH₂CH₂ | 2-trifluoromethyl-5-pyridyl |
| 792 | CH₂CH₂ | 2-pyrimidinyl |
| 793 | CH₂CH₂ | 3-pyrimidinyl |
| 794 | CH₂CH₂ | 4-pyrimidinyl |
| 795 | CH₂CH₂ | 2-pyrazinyl |
| 796 | CH₂CH₂ | 3-pyridazinyl |
| 797 | CH₂CH₂ | 4-pyridazinyl |
| 798 | CH₂CH₂ | 2-(2H-1,3-oxazinyl) |
| 799 | CH₂CH₂ | 2-(6H-1,3-oxazinyl) |
| 800 | CH₂CH₂ | 4-(6H-1,3-oxazinyl) |
| 801 | CH₂CH₂ | 6-(6H-1,3-oxazinyl) |
| 802 | CH₂CH₂ | [1,3,5]-2-triazinyl |
| 803 | CH₂CH₂ | [1,2,4]-3-triazinyl |
| 804 | CH₂CH₂ | [1,2,4]-5-triazinyl |
| 805 | CH₂CH₂ | [1,2,4]-6-triazinyl |
| 806 | —C≡C— | oxiranyl |
| 807 | —C≡C— | 3-methyl-2-oxiranyl |
| 808 | —C≡C— | 2-oxetanyl |
| 809 | —C≡C— | 3-hydroxy-3-methyl-2-oxetanyl |
| 810 | —C≡C— | 3-hydroxy-3-ethyl-2-oxetanyl |
| 811 | —C≡C— | 3-hydroxy-3-propyl-2-oxetanyl |
| 812 | —C≡C— | 3-hydroxy-3-butyl-2-oxetanyl |
| 813 | —C≡C— | 3-methoxy-3-methyl-2-oxetanyl |
| 814 | —C≡C— | 3-methoxy-3-ethyl-2-oxetanyl |
| 815 | —C≡C— | 3-methoxy-3-propyl-2-oxetanyl |
| 816 | —C≡C— | 3-methoxy-3-butyl-2-oxetanyl |
| 817 | —C≡C— | 3-trimethylsilyloxy-3-methyl-2-oxetanyl |
| 818 | —C≡C— | 3-trimethylsilyloxy-3-ethyl-2-oxetanyl |
| 819 | —C≡C— | 3-trimethylsilyloxy-3-propyl-2-oxetanyl |
| 820 | —C≡C— | 3-trimethylsilyloxy-3-butyl-2-oxetanyl |
| 821 | —C≡C— | 3-oxetanyl |
| 822 | —C≡C— | 2-furyl |
| 823 | —C≡C— | 4,5-dihydro-2-furyl |
| 824 | —C≡C— | 2,3-dihydro-2-furyl |
| 825 | —C≡C— | 3-furyl |
| 826 | —C≡C— | 4,5-dihydro-3-furyl |
| 827 | —C≡C— | 2,3-dihydro-3-furyl |
| 828 | —C≡C— | 2-thienyl |
| 829 | —C≡C— | 4,5-dihydro-2-thienyl |
| 830 | —C≡C— | 2,3-dihydro-2-thienyl |
| 831 | —C≡C— | 5-chloro-2-thienyl |
| 832 | —C≡C— | 5-methyl-2-thienyl |
| 833 | —C≡C— | 3-thienyl |
| 834 | —C≡C— | 4,5-dihydro-3-thienyl |
| 835 | —C≡C— | 2,3-dihydro-3-thienyl |
| 836 | —C≡C— | 2-pyrrolyl |
| 837 | —C≡C— | 2,5-dihydro-2-pyrrolyl |
| 838 | —C≡C— | 3-pyrrole |
| 839 | —C≡C— | 2,5-dihydro-3-pyrrolyl |
| 840 | —C≡C— | 3-isoxazolyl |
| 841 | —C≡C— | 4-methyl-3-isoxazolyl |
| 842 | —C≡C— | 5-methyl-3-isoxazolyl |
| 843 | —C≡C— | 4,5-dimethyl-3-isoxazolyl |
| 844 | —C≡C— | 4,5-dihydro-3-isoxazolyl |
| 845 | —C≡C— | 4-methyl-4,5-dihydro-3-isoxazolyl |
| 846 | —C≡C— | 5-methyl-4,5-dihydro-3-isoxazolyl |
| 847 | —C≡C— | 4,5-dimethyl-4,5-dihydro-3-isoxazolyl |

TABLE A-continued

| No. | X¹ | Het |
|---|---|---|
| 848 | —C≡C— | 4-isoxazolyl |
| 849 | —C≡C— | 3-methyl-4-isoxazolyl |
| 850 | —C≡C— | 5-methyl-4-isoxazolyl |
| 851 | —C≡C— | 5-cyclopropyl-4-isoxazolyl |
| 852 | —C≡C— | 5-phenyl-4-isoxazolyl |
| 853 | —C≡C— | 3,5-dimethyl-4-isoxazolyl |
| 854 | —C≡C— | 4,5-dihydro-4-isoxazolyl |
| 855 | —C≡C— | 3-methyl-4,5-dihydro-4-isoxazolyl |
| 856 | —C≡C— | 5-methyl-4,5-dihydro-4-isoxazolyl |
| 857 | —C≡C— | 3,5-dimethyl-4,5-dihydro-4-isoxazolyl |
| 858 | —C≡C— | 5-isoxazolyl |
| 859 | —C≡C— | 3-methyl-5-isoxazolyl |
| 860 | —C≡C— | 4-methyl-5-isoxazolyl |
| 861 | —C≡C— | 3,4-dimethyl-5-isoxazolyl |
| 862 | —C≡C— | 4,5-dihydro-5-isoxazolyl |
| 863 | —C≡C— | 3-methyl-4,5-dihydro-5-isoxazolyl |
| 864 | —C≡C— | 4-methyl-4,5-dihydro-5-isoxazolyl |
| 865 | —C≡C— | 3,4-dimethyl-4,5-dihydro-5-isoxazolyl |
| 866 | —C≡C— | 3-isothiazolyl |
| 867 | —C≡C— | 4-methyl-3-isothiazolyl |
| 868 | —C≡C— | 5-methyl-3-isothiazolyl |
| 869 | —C≡C— | 4-isothiazolyl |
| 870 | —C≡C— | 3-methyl-4-isothiazolyl |
| 871 | —C≡C— | 5-methyl-4-isothiazolyl |
| 872 | —C≡C— | 5-isothiazolyl |
| 873 | —C≡C— | 3-methyl-5-isothiazolyl |
| 874 | —C≡C— | 4-methyl-5-isothiazolyl |
| 875 | —C≡C— | 2-oxazolyl |
| 876 | —C≡C— | 4-oxazolyl |
| 877 | —C≡C— | 5-oxazolyl |
| 878 | —C≡C— | 2-thiazolyl |
| 879 | —C≡C— | 4-thiazolyl |
| 880 | —C≡C— | 5-thiazolyl |
| 881 | —C≡C— | 3-pyrazolyl |
| 882 | —C≡C— | 4-pyrazolyl |
| 883 | —C≡C— | 1-methyl-3-pyrazolyl |
| 884 | —C≡C— | 1-methyl-4-pyrazolyl |
| 885 | —C≡C— | 1-methyl-5-pyrazolyl |
| 886 | —C≡C— | 2-imidazolyl |
| 887 | —C≡C— | 1-methyl-2-imidazolyl |
| 888 | —C≡C— | 5-methyl-[1,3,4]-2-oxadiazolyl |
| 889 | —C≡C— | 5-methyl-[1,2,4]-3-oxadiazolyl |
| 890 | —C≡C— | 5-methyl-[1,3,4]-2-thiadiazolyl |
| 891 | —C≡C— | 5-methyl-[1,2,4]-3-thiadiazolyl |
| 892 | —C≡C— | [1,2,4]-3-triazolyl |
| 893 | —C≡C— | [1,2,3]-4-triazolyl |
| 894 | —C≡C— | 2-pyridyl |
| 895 | —C≡C— | 6-chloro-2-pyridyl |
| 896 | —C≡C— | 6-methoxy-2-pyridyl |
| 897 | —C≡C— | 6-trifluoromethyl-2-pyridyl |
| 898 | —C≡C— | 3-pyridyl |
| 899 | —C≡C— | 2-chloro-3-pyridyl |
| 900 | —C≡C— | 2-methoxy-3-pyridyl |
| 901 | —C≡C— | 4-pyridyl |
| 902 | —C≡C— | 2-chloro-4-pyridyl |
| 903 | —C≡C— | 2-methoxy-4-pyridyl |
| 904 | —C≡C— | 2-ethoxy-4-pyridyl |
| 905 | —C≡C— | 2-methylthio-4-pyridyl |
| 906 | —C≡C— | 2-trifluoromethyl-5-pyridyl |
| 907 | —C≡C— | 2-pyrimidinyl |
| 908 | —C≡C— | 3-pyrimidinyl |
| 909 | —C≡C— | 4-pyrimidinyl |
| 910 | —C≡C— | 2-pyrazinyl |
| 911 | —C≡C— | 3-pyridazinyl |
| 912 | —C≡C— | 4-pyridazinyl |
| 913 | —C≡C— | 2-(2H-1,3-oxazinyl) |
| 914 | —C≡C— | 2-(6H-1,3-oxazinyl) |
| 915 | —C≡C— | 4-(6H-1,3-oxazinyl) |
| 916 | —C≡C— | 6-(6H-1,3-oxazinyl) |
| 917 | —C≡C— | [1,3,5]-2-triazinyl |
| 918 | —C≡C— | [1,2,4]-3-triazinyl |
| 919 | —C≡C— | [1,2,4]-5-triazinyl |
| 920 | —C≡C— | [1,2,4]-6-triazinyl |

Tables 1–144 below are based on the 4-benzoylpyrazoles of the formula Ib.

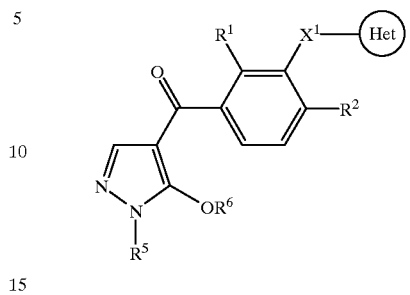

Table 1: Compounds 1.1–1.920

Compounds of the formula Ib in which $R^1$ is chlorine and $R^2$ is chlorine, $R^5$ is methyl and $R^6$ is hydrogen and where for each individual compound the substituents $X^1$ and Het correspond in each case to one line of Table A.

Table 2: Compounds 2.1–2.920

Compounds of the formula Ib in which $R^1$ is chlorine and $R^2$ is chlorine, $R^5$ is ethyl and $R^6$ is hydrogen and where for each individual compound the substituents $X^1$ and Het correspond in each case to one line of Table A.

Table 3: Compounds 3.1–3.920

Compounds of the formula Ib in which $R^1$ is chlorine and $R^2$ is chlorine, $R^5$ is n-propyl and $R^6$ is hydrogen and where for each individual compound the substituents $X^1$ and Het correspond in each case to one line of Table A.

Table 4: Compounds 4.1–4.920

Compounds of the formula Ib in which $R^1$ is chlorine and $R^2$ is chlorine, $R^5$ is methyl and $R^6$ is methyl and where for each individual compound the substituents $X^1$ and Het correspond in each case to one line of Table A.

Table 5: Compounds 5.1–5.920

Compounds of the formula Ib in which $R^1$ is chlorine and $R^2$ is chlorine, $R^5$ is ethyl and $R^6$ is methyl and where for each individual compound the substituents $X^1$ and Het correspond in each case to one line of Table A.

Table 6: Compounds 6.1–6.920

Compounds of the formula Ib in which $R^1$ is chlorine and $R^2$ is chlorine, $R^5$ is n-propyl and $R^6$ is methyl and where for each individual compound the substituents $X^1$ and Het correspond in each case to one line of Table A.

Table 7: Compounds 7.1–7.920

Compounds of the formula Ib in which $R^1$ is chlorine and $R^2$ is chlorine, $R^5$ is methyl and $R^6$ is ethyl and where for each individual compound the substituents $X^1$ and Het correspond in each case to one line of Table A.

Table 8: Compounds 8.1–8.920

Compounds of the formula Ib in which $R^1$ is chlorine and $R^2$ is chlorine, $R^5$ is ethyl and $R^6$ is ethyl and where for each individual compound the substituents $X^1$ and Het correspond in each case to one line of Table A.

Table 9: Compounds 9.1–9.920

Compounds of the formula Ib in which $R^1$ is chlorine and $R^2$ is chlorine, $R^5$ is n-propyl and $R^6$ is ethyl and where for each individual compound the substituents $X^1$ and Het correspond in each case to one line of Table A.

Table 10: Compounds 10.1–10.920

Compounds of the formula Ib in which $R^1$ is chlorine and $R^2$ is chlorine, $R^5$ is methyl and $R^6$ is methylcarbonyl and where for each individual compound the substituents $X^1$ and Het correspond in each case to one line of Table A.

Table 11: Compounds 11.1–11.920

Compounds of the formula Ib in which $R^1$ is chlorine and $R^2$ is chlorine, $R^5$ is ethyl and $R^6$ is methylcarbonyl and where for each individual compound the substituents $X^1$ and Het correspond in each case to one line of Table A.

Table 12: Compounds 12.1–12.920

Compounds of the formula Ib in which $R^1$ is chlorine and $R^2$ is chlorine, $R^5$ is n-propyl and $R^6$ is methylcarbonyl and where for each individual compound the substituents $X^1$ and Het correspond in each case to one line of Table A.

Table 13: Compounds 13.1–13.920

Compounds of the formula Ib in which $R^1$ is chlorine and $R^2$ is chlorine, $R^5$ is methyl and $R^6$ is ethylcarbonyl and where for each individual compound the substituents $X^1$ and Het correspond in each case to one line of Table A.

Table 14: Compounds 14.1–14.920

Compounds of the formula Ib in which $R^1$ is chlorine and $R^2$ is chlorine, $R^5$ is ethyl and $R^6$ is ethylcarbonyl and where for each individual compound the substituents $X^1$ and Het correspond in each case to one line of Table A.

Table 15: Compounds 15.1–15.920

Compounds of the formula Ib in which $R^1$ is chlorine and $R^2$ is chlorine, $R^5$ is n-propyl and $R^6$ is ethylcarbonyl and where for each individual compound the substituents $X^1$ and Het correspond in each case to one line of Table A.

Table 16: Compounds 16.1–16.920

Compounds of the formula Ib in which $R^1$ is chlorine and $R^2$ is chlorine, $R^5$ is methyl and $R^6$ is methylsulfonyl and where for each individual compound the substituents $X^1$ and Het correspond in each case to one line of Table A.

Table 17: Compounds 17.1–17.920

Compounds of the formula Ib in which $R^1$ is chlorine and $R^2$ is chlorine, $R^5$ is ethyl and $R^6$ is methylsulfonyl and where for each individual compound the substituents $X^1$ and Het correspond in each case to one line of Table A.

Table 18: Compounds 18.1–18.920

Compounds of the formula Ib in which $R^1$ is chlorine and $R^2$ is chlorine, $R^5$ is n-propyl and $R^6$ is methylsulfonyl and where for each individual compound the substituents $X^1$ and Het correspond in each case to one line of Table A.

Table 19: Compounds 19.1–19.920

Compounds of the formula Ib in which $R^1$ is chlorine and $R^2$ is chlorine, $R^5$ is methyl and $R^6$ is ethylsulfonyl and where for each individual compound the substituents $X^1$ and Het correspond in each case to one line of Table A.

Table 20: Compounds 20.1–20.920

Compounds of the formula Ib in which $R^1$ is chlorine and $R^2$ is chlorine, $R^5$ is ethyl and $R^6$ is ethylsulfonyl and where for each individual compound the substituents $X^1$ and Het correspond in each case to one line of Table A.

Table 21: Compounds 21.1–21.920

Compounds of the formula Ib in which $R^1$ is chlorine and $R^2$ is chlorine, $R^5$ is n-propyl and $R^6$ is ethylsulfonyl and where for each individual compound the substituents $X^1$ and Het correspond in each case to one line of Table A.

Table 22: Compounds 22.1–22.920

Compounds of the formula Ib in which $R^1$ is chlorine and $R^2$ is chlorine, $R^5$ is methyl and $R^6$ is 4-methylphenylsulfonyl and where for each individual compound the substituents $X^1$ and Het correspond in each case to one line of Table A.

Table 23: Compounds 23.1–23.920

Compounds of the formula Ib in which $R^1$ is chlorine and $R^2$ is chlorine, $R^5$ is ethyl and $R^6$ is 4-methylphenylsulfonyl and where for each individual compound the substituents $X^1$ and Het correspond in each case to one line of Table A.

Table 24: Compounds 24.1–24.920

Compounds of the formula Ib in which $R^1$ is chlorine and $R^2$ is chlorine, $R^5$ is n-propyl and $R^6$ is 4-methylphenylsulfonyl and where for each individual compound the substituents $X^1$ and Het correspond in each case to one line of Table A.

Table 25: Compounds 25.1–25.920

Compounds of the formula Ib in which $R^1$ is chlorine and $R^2$ is methylsulfonyl, $R^5$ is methyl and $R^6$ is hydrogen and where for each individual compound the substituents $X^1$ and Het correspond in each case to one line of Table A.

Table 26: Compounds 26.1–26.920

Compounds of the formula Ib in which $R^1$ is chlorine and $R^2$ is methylsulfonyl, $R^5$ is ethyl and $R^6$ is hydrogen and where for each individual compound the substituents $X^1$ and Het correspond in each case to one line of Table A.

Table 27: Compounds 27.1–27.920

Compounds of the formula Ib in which $R^1$ is chlorine and $R^2$ is methylsulfonyl, $R^5$ is n-propyl and $R^6$ is hydrogen and where for each individual compound the substituents $X^1$ and Het correspond in each case to one line of Table A.

Table 28: Compounds 28.1–28.920

Compounds of the formula Ib in which $R^1$ is chlorine and $R^2$ is methylsulfonyl, $R^5$ is methyl and $R^6$ is methyl and where for each individual compound the substituents $X^1$ and Het correspond in each case to one line of Table A.

Table 29: Compounds 29.1–29.920

Compounds of the formula Ib in which $R^1$ is chlorine and $R^2$ is methylsulfonyl, $R^5$ is ethyl and $R^6$ is methyl and where for each individual compound the substituents $X^1$ and Het correspond in each case to one line of Table A.

Table 30: Compounds 30.1–30.920

Compounds of the formula Ib in which $R^1$ is chlorine and $R^2$ is methylsulfonyl, $R^5$ is n-propyl and $R^6$ is methyl and where for each individual compound the substituents $X^1$ and Het correspond in each case to one line of Table A.

Table 31: Compounds 31.1–31.920

Compounds of the formula Ib in which $R^1$ is chlorine and $R^2$ is methylsulfonyl, $R^5$ is methyl and $R^6$ is ethyl and where for each individual compound the substituents $X^1$ and Het correspond in each case to one line of Table A.

Table 32: Compounds 32.1–32.920

Compounds of the formula Ib in which $R^1$ is chlorine and $R^2$ is methylsulfonyl, $R^5$ is ethyl and $R^6$ is ethyl and where for each individual compound the substituents $X^1$ and Het correspond in each case to one line of Table A.

Table 33: Compounds 33.1–33.920

Compounds of the formula Ib in which $R^1$ is chlorine and $R^2$ is methylsulfonyl, $R^5$ is n-propyl and $R^6$ is ethyl and where for each individual compound the substituents $X^1$ and Het correspond in each case to one line of Table A.

Table 34: Compounds 34.1–34.920

Compounds of the formula Ib in which $R^1$ is chlorine and $R^2$ is methylsulfonyl, $R^5$ is methyl and $R^6$ is methylcarbonyl and where for each individual compound the substituents $X^1$ and Het correspond in each case to one line of Table A.

Table 35: Compounds 35.1–35.920

Compounds of the formula Ib in which $R^1$ is chlorine and $R^2$ is methylsulfonyl, $R^5$ is ethyl and $R^6$ is methylcarbonyl and where for each individual compound the substituents $X^1$ and Het correspond in each case to one line of Table A.

Table 36: Compounds 36.1–36.920

Compounds of the formula Ib in which $R^1$ is chlorine and $R^2$ is methylsulfonyl, $R^5$ is n-propyl and $R^6$ is methylcarbonyl and where for each individual compound the substituents $X^1$ and Het correspond in each case to one line of Table A.

Table 37: Compounds 37.1–37.920

Compounds of the formula Ib in which $R^1$ is chlorine and $R^2$ is methylsulfonyl, $R^5$ is methyl and $R^6$ is ethylcarbonyl and where for each individual compound the substituents $X^1$ and Het correspond in each case to one line of Table A.

Table 38: Compounds 38.1–38.920

Compounds of the formula Ib in which $R^1$ is chlorine and $R^2$ is methylsulfonyl, $R^5$ is ethyl and $R^6$ is ethylcarbonyl and where for each individual compound the substituents $X^1$ and Het correspond in each case to one line of Table A.

Table 39: Compounds 39.1–39.920

Compounds of the formula Ib in which $R^1$ is chlorine and $R^2$ is methylsulfonyl, $R^5$ is n-propyl and $R^6$ is ethylcarbonyl and where for each individual compound the substituents $X^1$ and Het correspond in each case to one line of Table A.

Table 40: Compounds 40.1–40.920

Compounds of the formula Ib in which $R^1$ is chlorine and $R^2$ is methylsulfonyl, $R^5$ is methyl and $R^6$ is methylsulfonyl and where for each individual compound the substituents $X^1$ and Het correspond in each case to one line of Table A.

Table 41: Compounds 41.1–41.920

Compounds of the formula Ib in which $R^1$ is chlorine and $R^2$ is methylsulfonyl, $R^5$ is ethyl and $R^6$ is methylsulfonyl and where for each individual compound the substituents $X^1$ and Het correspond in each case to one line of Table A.

Table 42: Compounds 42.1–42.920

Compounds of the formula Ib in which $R^1$ is chlorine and $R^2$ is methylsulfonyl, $R^5$ is n-propyl and $R^6$ is methylsulfonyl and where for each individual compound the substituents $X^1$ and Het correspond in each case to one line of Table A.

Table 43: Compounds 43.1–43.920

Compounds of the formula Ib in which $R^1$ is chlorine and $R^2$ is methylsulfonyl, $R^5$ is methyl and $R^6$ is ethylsulfonyl and where for each individual compound the substituents $X^1$ and Het correspond in each case to one line of Table A.

Table 44: Compounds 44.1–44.920

Compounds of the formula Ib in which $R^1$ is chlorine and $R^2$ is methylsulfonyl, $R^5$ is ethyl and $R^6$ is ethylsulfonyl and where for each individual compound the substituents $X^1$ and Het correspond in each case to one line of Table A.

Table 45: Compounds 45.1–45.920

Compounds of the formula Ib in which $R^1$ is chlorine and $R^2$ is methylsulfonyl, $R^5$ is n-propyl and $R^6$ is ethylsulfonyl and where for each individual compound the substituents $X^1$ and Het correspond in each case to one line of Table A.

Table 46: Compounds 46.1–46.920

Compounds of the formula Ib in which $R^1$ is chlorine and $R^2$ is methylsulfonyl, $R^5$ is methyl and $R^6$ is 4-methylphenylsulfonyl and where for each individual compound the substituents $X^1$ and Het correspond in each case to one line of Table A.

Table 47: Compounds 47.1–47.920

Compounds of the formula Ib in which $R^1$ is chlorine and $R^2$ is methylsulfonyl, $R^5$ is ethyl and $R^6$ is 4-methylphenylsulfonyl and where for each individual compound the substituents $X^1$ and Het correspond in each case to one line of Table A.

Table 48: Compounds 48.1–48.920

Compounds of the formula Ib in which $R^1$ is chlorine and $R^2$ is methylsulfonyl, $R^5$ is n-propyl and $R^6$ is 4-methylphenylsulfonyl and where for each individual compound the substituents $X^1$ and Het correspond in each case to one line of Table A.

Table 49: Compounds 49.1–49.920

Compounds of the formula Ib in which $R^1$ is chlorine and $R^2$ is trifluoromethyl, $R^5$ is methyl and $R^6$ is hydrogen and where for each individual compound the substituents $X^1$ and Het correspond in each case to one line of Table A.

Table 50: Compounds 50.1–50.920

Compounds of the formula Ib in which $R^1$ is chlorine and $R^2$ is trifluoromethyl, $R^5$ is ethyl and $R^6$ is hydrogen and where for each individual compound the substituents $X^1$ and Het correspond in each case to one line of Table A.

Table 51: Compounds 51.1–51.920

Compounds of the formula Ib in which $R^1$ is chlorine and $R^2$ is trifluoromethyl, $R^5$ is n-propyl and $R^6$ is hydrogen and where for each individual compound the substituents $X^1$ and Het correspond in each case to one line of Table A.

Table 52: Compounds 52.1–52.920

Compounds of the formula Ib in which $R^1$ is chlorine and $R^2$ is trifluoromethyl, $R^5$ is methyl and $R^6$ is methyl and where for each individual compound the substituents $X^1$ and Het correspond in each case to one line of Table A.

Table 53: Compounds 53.1–53.920

Compounds of the formula Ib in which $R^1$ is chlorine and $R^2$ is trifluoromethyl, $R^5$ is ethyl and $R^6$ is methyl and where for each individual compound the substituents $X^1$ and Het correspond in each case to one line of Table A.

Table 54: Compounds 54.1–54.920

Compounds of the formula Ib in which $R^1$ is chlorine and $R^2$ is trifluoromethyl, $R^5$ is n-propyl and $R^6$ is methyl and where for each individual compound the substituents $X^1$ and Het correspond in each case to one line of Table A.

Table 55: Compounds 55.1–55.920

Compounds of the formula Ib in which $R^1$ is chlorine and $R^2$ is trifluoromethyl, $R^5$ is methyl and $R^6$ is ethyl and where for each individual compound the substituents $X^1$ and Het correspond in each case to one line of Table A.

Table 56: Compounds 56.1–56.920

Compounds of the formula Ib in which $R^1$ is chlorine and $R^2$ is trifluoromethyl, $R^5$ is ethyl and $R^6$ is ethyl and where for each individual compound the substituents $X^1$ and Het correspond in each case to one line of Table A.

Table 57: Compounds 57.1–57.920

Compounds of the formula Ib in which $R^1$ is chlorine and $R^2$ is trifluoromethyl, $R^5$ is n-propyl and $R^6$ is ethyl and where for each individual compound the substituents $X^1$ and Het correspond in each case to one line of Table A.

Table 58: Compounds 58.1–58.920

Compounds of the formula Ib in which $R^1$ is chlorine and $R^2$ is trifluoromethyl, $R^5$ is methyl and $R^6$ is methylcarbonyl and where for each individual compound the substituents $X^1$ and Het correspond in each case to one line of Table A.

Table 59: Compounds 59.1–59.920

Compounds of the formula Ib in which $R^1$ is chlorine and $R^2$ is trifluoromethyl, $R^5$ is ethyl and $R^6$ is methylcarbonyl and where for each individual compound the substituents $X^1$ and Het correspond in each case to one line of Table A.

Table 60: Compounds 60.1–60.920

Compounds of the formula Ib in which $R^1$ is chlorine and $R^2$ is chlorine, $R^5$ is n-propyl and $R^6$ is methylcarbonyl and where for each individual compound the substituents $X^1$ and Het correspond in each case to one line of Table A.

Table 61: Compounds 61.1–61.920

Compounds of the formula Ib in which $R^1$ is chlorine and $R^2$ is trifluoromethyl, $R^5$ is methyl and $R^6$ is ethylcarbonyl and where for each individual compound the substituents $X^1$ and Het correspond in each case to one line of Table A.

Table 62: Compounds 62.1–62.920

Compounds of the formula Ib in which $R^1$ is chlorine and $R^2$ is trifluoromethyl, $R^5$ is ethyl and $R^6$ is ethylcarbonyl and where for each individual compound the substituents $X^1$ and Het correspond in each case to one line of Table A.

Table 63: Compounds 63.1–63.920

Compounds of the formula Ib in which $R^1$ is chlorine and $R^2$ is trifluoromethyl, $R^5$ is n-propyl and $R^6$ is ethylcarbonyl and where for each individual compound the substituents $X^1$ and Het correspond in each case to one line of Table A.

Table 64: Compounds 64.1–64.920

Compounds of the formula Ib in which $R^1$ is chlorine and $R^2$ is trifluoromethyl, $R^5$ is methyl and $R^6$ is methylsulfonyl and where for each individual compound the substituents $X^1$ and Het correspond in each case to one line of Table A.

Table 65: Compounds 65.1–65.920

Compounds of the formula Ib in which $R^1$ is chlorine and $R^2$ is trifluoromethyl, $R^5$ is ethyl and $R^6$ is methylsulfonyl and where for each individual compound the substituents $X^1$ and Het correspond in each case to one line of Table A.

Table 66: Compounds 66.1–66.920

Compounds of the formula Ib in which $R^1$ is chlorine and $R^2$ is trifluoromethyl, $R^5$ is n-propyl and $R^6$ is methylsulfonyl and where for each individual compound the substituents $X^1$ and Het correspond in each case to one line of Table A.

Table 67: Compounds 67.1–67.920

Compounds of the formula Ib in which $R^1$ is chlorine and $R^2$ is trifluoromethyl, $R^5$ is methyl and $R^6$ is ethylsulfonyl and where for each individual compound the substituents $X^1$ and Het correspond in each case to one line of Table A.

Table 68: Compounds 68.1–68.920

Compounds of the formula Ib in which $R^1$ is chlorine and $R^2$ is trifluoromethyl, $R^5$ is ethyl and $R^6$ is ethylsulfonyl and where for each individual compound the substituents $X^1$ and Het correspond in each case to one line of Table A.

Table 69: Compounds 69.1–69.920

Compounds of the formula Ib in which $R^1$ is chlorine and $R^2$ is trifluoromethyl, $R^5$ is n-propyl and $R^6$ is ethylsulfonyl and where for each individual compound the substituents $X^1$ and Het correspond in each case to one line of Table A.

Table 70: Compounds 70.1–70.920

Compounds of the formula Ib in which $R^1$ is chlorine and $R^2$ is trifluoromethyl, $R^5$ is methyl and $R^6$ is 4-methylphenylsulfonyl and where for each individual com- Table 71: Compounds 71.1–71.920

Compounds of the formula Ib in which $R^1$ is chlorine and $R^2$ is trifluoromethyl, $R^5$ is ethyl and $R^6$ is 4-methylphenylsulfonyl and where for each individual compound the substituents $X^1$ and Het correspond in each case to one line of Table A.

Table 72: Compounds 72.1–72.920

Compounds of the formula Ib in which $R^1$ is chlorine and $R^2$ is trifluoromethyl, $R^5$ is n-propyl and $R^6$ is 4-methylphenylsulfonyl and where for each individual compound the substituents $X^1$ and Het correspond in each case to one line of Table A.

Table 73: Compounds 73.1–73.920

Compounds of the formula Ib in which $R^1$ is methyl and $R^2$ is chlorine, $R^5$ is methyl and $R^6$ is hydrogen and where for each individual compound the substituents $X^1$ and Het correspond in each case to one line of Table A.

Table 74: Compounds 74.1–74.920

Compounds of the formula Ib in which $R^1$ is methyl and $R^2$ is chlorine, $R^5$ is ethyl and $R^6$ is hydrogen and where for each individual compound the substituents $X^1$ and Het correspond in each case to one line of Table A.

Table 75: Compounds 75.1–75.920

Compounds of the formula Ib in which $R^1$ is methyl and $R^2$ is chlorine, $R^5$ is n-propyl and $R^6$ is hydrogen and where for each individual compound the substituents $X^1$ and Het correspond in each case to one line of Table A.

Table 76: Compounds 76.1–76.920

Compounds of the formula Ib in which $R^1$ is methyl and $R^2$ is chlorine, $R^5$ is methyl and $R^6$ is methyl and where for each individual compound the substituents $X^1$ and Het correspond in each case to one line of Table A.

Table 77: Compounds 77.1–77.920

Compounds of the formula Ib in which $R^1$ is methyl and $R^2$ is chlorine, $R^5$ is ethyl and $R^6$ is methyl and where for each individual compound the substituents $X^1$ and Het correspond in each case to one line of Table A.

Table 78: Compounds 78.1–78.920

Compounds of the formula Ib in which $R^1$ is methyl and $R^2$ is chlorine, $R^5$ is n-propyl and $R^6$ is methyl and where for each individual compound the substituents $X^1$ and Het correspond in each case to one line of Table A.

Table 79: Compounds 79.1–79.920

Compounds of the formula Ib in which $R^1$ is methyl and $R^2$ is chlorine, $R^5$ is methyl and $R^6$ is ethyl and where for each individual compound the substituents $X^1$ and Het correspond in each case to one line of Table A.

Table 80: Compounds 80.1–80.920

Compounds of the formula Ib in which $R^1$ is methyl and $R^2$ is chlorine, $R^5$ is ethyl and $R^6$ is ethyl and where for each individual compound the substituents $X^1$ and Het correspond in each case to one line of Table A.

Table 81: Compounds 81.1–81.920

Compounds of the formula Ib in which $R^1$ is methyl and $R^2$ is chlorine, $R^5$ is n-propyl and $R^6$ is ethyl and where for each individual compound the substituents $X^1$ and Het correspond in each case to one line of Table A.

Table 82: Compounds 82.1–82.920

Compounds of the formula Ib in which $R^1$ is methyl and $R^2$ is chlorine, $R^5$ is methyl and $R^6$ is methylcarbonyl and where for each individual compound the substituents $X^1$ and Het correspond in each case to one line of Table A.

Table 83: Compounds 83.1–83.920

Compounds of the formula Ib in which $R^1$ is methyl and $R^2$ is chlorine, $R^5$ is ethyl and $R^6$ is methylcarbonyl and where for each individual compound the substituents $X^1$ and Het correspond in each case to one line of Table A.

Table 84: Compounds 84.1–84.920

Compounds of the formula Ib in which $R^1$ is methyl and $R^2$ is chlorine, $R^5$ is n-propyl and $R^6$ is methylcarbonyl and where for each individual compound the substituents $X^1$ and Het correspond in each case to one line of Table A.

Table 85: Compounds 85.1–85.920

Compounds of the formula Ib in which $R^1$ is methyl and $R^2$ is chlorine, $R^5$ is methyl and $R^6$ is ethylcarbonyl and where for each individual compound the substituents $X^1$ and Het correspond in each case to one line of Table A.

Table 86: Compounds 86.1–86.920

Compounds of the formula Ib in which $R^1$ is methyl and $R^2$ is chlorine, $R^5$ is ethyl and $R^6$ is ethylcarbonyl and where for each individual compound the substituents $X^1$ and Het correspond in each case to one line of Table A.

Table 87: Compounds 87.1–87.920

Compounds of the formula Ib in which $R^1$ is methyl and $R^2$ is chlorine, $R^5$ is n-propyl and $R^6$ is ethylcarbonyl and where for each individual compound the substituents $X^1$ and Het correspond in each case to one line of Table A.

Table 88: Compounds 88.1–88.920

Compounds of the formula Ib in which $R^1$ is methyl and $R^2$ is chlorine, $R^5$ is methyl and $R^6$ is methylsulfonyl and where for each individual compound the substituents $X^1$ and Het correspond in each case to one line of Table A.

Table 89: Compounds 89.1–89.920

Compounds of the formula Ib in which $R^1$ is methyl and $R^2$ is chlorine, $R^5$ is ethyl and $R^6$ is methylsulfonyl and where for each individual compound the substituents $X^1$ and Het correspond in each case to one line of Table A.

Table 90: Compounds 90.1–90.920

Compounds of the formula Ib in which $R^1$ is methyl and $R^2$ is chlorine, $R^5$ is n-propyl and $R^6$ is methylsulfonyl and where for each individual compound the substituents $X^1$ and Het correspond in each case to one line of Table A.

Table 91: Compounds 91.1–91.920

Compounds of the formula Ib in which $R^1$ is methyl and $R^2$ is chlorine, $R^5$ is methyl and $R^6$ is ethylsulfonyl and where for each individual compound the substituents $X^1$ and Het correspond in each case to one line of Table A.

Table 92: Compounds 92.1–92.920

Compounds of the formula Ib in which $R^1$ is methyl and $R^2$ is chlorine, $R^5$ is ethyl and $R^6$ is ethylsulfonyl and where for each individual compound the substituents $X^1$ and Het correspond in each case to one line of Table A.

Table 93: Compounds 93.1–93.920

Compounds of the formula Ib in which $R^1$ is methyl and $R^2$ is chlorine, $R^5$ is n-propyl and $R^6$ is ethylsulfonyl and where for each individual compound the substituents $X^1$ and Het correspond in each case to one line of Table A.

Table 94: Compounds 94.1–94.920

Compounds of the formula Ib in which $R^1$ is methyl and $R^2$ is chlorine, $R^5$ is methyl and $R^6$ is 4-methylphenylsulfonyl and where for each individual compound the substituents $X^1$ and Het correspond in each case to one line of Table A.

Table 95: Compounds 95.1–95.920

Compounds of the formula Ib in which $R^1$ is methyl and $R^2$ is chlorine, $R^5$ is ethyl and $R^6$ is 4-methylphenylsulfonyl and where for each individual compound the substituents $X^1$ and Het correspond in each case to one line of Table A.

Table 96: Compounds 96.1–96.920

Compounds of the formula Ib in which $R^1$ is methyl and $R^2$ is chlorine, $R^5$ is n-propyl and $R^6$ is 4-methylphenylsulfonyl and where for each individual compound the substituents $X^1$ and Het correspond in each case to one line of Table A.

Table 97: Compounds 97.1–97.920

Compounds of the formula Ib in which $R^1$ is methyl and $R^2$ is methylsulfonyl, $R^5$ is methyl and $R^6$ is hydrogen and where for each individual compound the substituents $X^1$ and Het correspond in each case to one line of Table A.

Table 98: Compounds 98.1–98.920

Compounds of the formula Ib in which $R^1$ is methyl and $R^2$ is methylsulfonyl, $R^5$ is ethyl and $R^6$ is hydrogen and where for each individual compound the substituents $X^1$ and Het correspond in each case to one line of Table A.

Table 99: Compounds 99.1–99.920

Compounds of the formula Ib in which $R^1$ is methyl and $R^2$ is methylsulfonyl, $R^5$ is n-propyl and $R^6$ is hydrogen and where for each individual compound the substituents $X^1$ and Het correspond in each case to one line of Table A.

Table 100: Compounds 100.1–100.920

Compounds of the formula Ib in which $R^1$ is methyl and $R^2$ is methylsulfonyl, $R^5$ is methyl and $R^6$ is methyl and where for each individual compound the substituents $X^1$ and Het correspond in each case to one line of Table A.

Table 101: Compounds 101.1–101.920

Compounds of the formula Ib in which $R^1$ is methyl and $R^2$ is methylsulfonyl, $R^5$ is ethyl and $R^6$ is methyl and where for each individual compound the substituents $X^1$ and Het correspond in each case to one line of Table A.

Table 102: Compounds 102.1–102.920

Compounds of the formula Ib in which $R^1$ is methyl and $R^2$ is methylsulfonyl, $R^5$ is n-propyl and $R^6$ is methyl and where for each individual compound the substituents $X^1$ and Het correspond in each case to one line of Table A.

Table 103: Compounds 103.1–103.920

Compounds of the formula Ib in which $R^1$ is methyl and $R^2$ is methylsulfonyl, $R^5$ is methyl and $R^6$ is ethyl and where for each individual compound the substituents $X^1$ and Het correspond in each case to one line of Table A.

Table 104: Compounds 104.1–104.920

Compounds of the formula Ib in which $R^1$ is methyl and $R^2$ is methylsulfonyl, $R^5$ is ethyl and $R^6$ is ethyl and where for each individual compound the substituents $X^1$ and Het correspond in each case to one line of Table A.

Table 105: Compounds 105.1–105.920

Compounds of the formula Ib in which $R^1$ is methyl and $R^2$ is methylsulfonyl, $R^5$ is n-propyl and $R^6$ is ethyl and where for each individual compound the substituents $X^1$ and Het correspond in each case to one line of Table A.

Table 106: Compounds 106.1–106.920

Compounds of the formula Ib in which $R^1$ is methyl and $R^2$ is methylsulfonyl, $R^5$ is methyl and $R^6$ is methylcarbonyl and where for each individual compound the substituents $X^1$ and Het correspond in each case to one line of Table A.

Table 107: Compounds 107.1–107.920

Compounds of the formula Ib in which $R^1$ is methyl and $R^2$ is methylsulfonyl, $R^5$ is ethyl and $R^6$ is methylcarbonyl and where for each individual compound the substituents $X^1$ and Het correspond in each case to one line of Table A.

Table 108: Compounds 108.1–108.920

Compounds of the formula Ib in which $R^1$ is methyl and $R^2$ is methylsulfonyl, $R^5$ is n-propyl and $R^6$ is methylcarbonyl and where for each individual compound the substituents $X^1$ and Het correspond in each case to one line of Table A.

Table 109: Compounds 109.1–109.920

Compounds of the formula Ib in which $R^1$ is methyl and $R^2$ is methylsulfonyl, $R^5$ is methyl and $R^6$ is ethylcarbonyl and where for each individual compound the substituents $X^1$ and Het correspond in each case to one line of Table A.

Table 110: Compounds 110.1–110.920

Compounds of the formula Ib in which $R^1$ is methyl and $R^2$ is methylsulfonyl, $R^5$ is ethyl and $R^6$ is ethylcarbonyl and where for each individual compound the substituents $X^1$ and Het correspond in each case to one line of Table A.

Table 111: Compounds 111.1–111.920

Compounds of the formula Ib in which $R^1$ is methyl and $R^2$ is methylsulfonyl, $R^5$ is n-propyl and $R^6$ is ethylcarbonyl and where for each individual compound the substituents $X^1$ and Het correspond in each case to one line of Table A.

Table 112: Compounds 112.1–112.920

Compounds of the formula Ib in which $R^1$ is methyl and $R^2$ is methylsulfonyl, $R^5$ is methyl and $R^6$ is methylsulfonyl and where for each individual compound the substituents $X^1$ and Het correspond in each case to one line of Table A.

Table 113: Compounds 113.1–113.920

Compounds of the formula Ib in which $R^1$ is methyl and $R^2$ is methylsulfonyl, $R^5$ is ethyl and $R^6$ is methylsulfonyl and where for each individual compound the substituents $X^1$ and Het correspond in each case to one line of Table A.

Table 114: Compounds 114.1–114.920

Compounds of the formula Ib in which $R^1$ is methyl and $R^2$ is methylsulfonyl, $R^5$ is n-propyl and $R^6$ is methylsulfonyl and where for each individual compound the substituents $X^1$ and Het correspond in each case to one line of Table A.

Table 115: Compounds 115.1–115.920

Compounds of the formula Ib in which $R^1$ is methyl and $R^2$ is methylsulfonyl, $R^5$ is methyl and $R^6$ is ethylsulfonyl and where for each individual compound the substituents $X^1$ and Het correspond in each case to one line of Table A.

Table 116: Compounds 116.1–116.920

Compounds of the formula Ib in which $R^1$ is methyl and $R^2$ is methylsulfonyl, $R^5$ is ethyl and $R^6$ is ethylsulfonyl and where for each individual compound the substituents $X^1$ and Het correspond in each case to one line of Table A.

Table 117: Compounds 117.1–117.920

Compounds of the formula Ib in which $R^1$ is methyl and $R^2$ is methylsulfonyl, $R^5$ is n-propyl and $R^6$ is ethylsulfonyl and where for each individual compound the substituents $X^1$ and Het correspond in each case to one line of Table A.

Table 118: Compounds 118.1–118.920

Compounds of the formula Ib in which $R^1$ is methyl and $R^2$ is methylsulfonyl, $R^5$ is methyl and $R^6$ is 4-methylphenylsulfonyl and where for each individual compound the substituents $X^1$ and Het correspond in each case to one line of Table A.

Table 119: Compounds 119.1–119.920

Compounds of the formula Ib in which $R^1$ is methyl and $R^2$ is methylsulfonyl, $R^5$ is ethyl and $R^6$ is 4-methylphenylsulfonyl and where for each individual compound the substituents $X^1$ and Het correspond in each case to one line of Table A.

Table 120: Compounds 120.1–120.920

Compounds of the formula Ib in which $R^1$ is methyl and $R^2$ is methylsulfonyl, $R^5$ is n-propyl and $R^6$ is 4-methylphenylsulfonyl where for each individual compound the substituents $X^1$ and Het correspond in each case to one line of Table A.

Table 121: Compounds 121.1–121.920

Compounds of the formula Ib in which $R^1$ is methyl and $R^2$ is trifluoromethyl, $R^5$ is methyl and $R^6$ is hydrogen and where for each individual compound the substituents $X^1$ and Het correspond in each case to one line of Table A.

Table 122: Compounds 122.1–122.920

Compounds of the formula Ib in which $R^1$ is methyl and $R^2$ is trifluoromethyl, $R^5$ is ethyl and $R^6$ is hydrogen and where for each individual compound the substituents $X^1$ and Het correspond in each case to one line of Table A.

Table 123: Compounds 123.1–123.920

Compounds of the formula Ib in which $R^1$ is methyl and $R^2$ is trifluoromethyl, $R^5$ is n-propyl and $R^6$ is hydrogen and where for each individual compound the substituents $X^1$ and Het correspond in each case to one line of Table A.

Table 124: Compounds 124.1–124.920

Compounds of the formula Ib in which $R^1$ is methyl and $R^2$ is trifluoromethyl, $R^5$ is methyl and $R^6$ is methyl and where for each individual compound the substituents $X^1$ and Het correspond in each case to one line of Table A.

Table 125: Compounds 12.1–125.920

Compounds of the formula Ib in which $R^1$ is methyl and $R^2$ is trifluoromethyl, $R^5$ is ethyl and $R^6$ is methyl and where for each individual compound the substituents $X^1$ and Het correspond in each case to one line of Table A.

Table 126: Compounds 126.1–126.920

Compounds of the formula Ib in which $R^1$ is methyl and $R^2$ is trifluoromethyl, $R^5$ is n-propyl and $R^6$ is methyl and where for each individual compound the substituents $X^1$ and Het correspond in each case to one line of Table A.

Table 127: Compounds 127.1–127.920

Compounds of the formula Ib in which $R^1$ is methyl and $R^2$ is trifluoromethyl, $R^5$ is methyl and $R^6$ is ethyl and where for each individual compound the substituents $X^1$ and Het correspond in each case to one line of Table A.

Table 128: Compounds 128.1–128.920

Compounds of the formula Ib in which $R^1$ is methyl and $R^2$ is trifluoromethyl, $R^5$ is ethyl and $R^6$ is ethyl and where for each individual compound the substituents $X^1$ and Het correspond in each case to one line of Table A.

Table 129: Compounds 129.1–129.920

Compounds of the formula Ib in which $R^1$ is methyl and $R^2$ is trifluoromethyl, $R^5$ is n-propyl and $R^6$ is ethyl and where for each individual compound the substituents $X^1$ and Het correspond in each case to one line of Table A.

Table 130: Compounds 130.1–130.920

Compounds of the formula Ib in which $R^1$ is methyl and $R^2$ is trifluoromethyl, $R^5$ is methyl and $R^6$ is methylcarbonyl and where for each individual compound the substituents $X^1$ and Het correspond in each case to one line of Table A.

Table 131: Compounds 131.1–131.920

Compounds of the formula Ib in which $R^1$ is methyl and $R^2$ is trifluoromethyl, $R^5$ is ethyl and $R^6$ is methylcarbonyl and where for each individual compound the substituents $X^1$ and Het correspond in each case to one line of Table A.

Table 132: Compounds 132.1–132.920

Compounds of the formula Ib in which $R^1$ is methyl and $R^2$ is trifluoromethyl, $R^5$ is n-propyl and $R^6$ is methylcarbonyl and where for each individual compound the substituents $X^1$ and Het correspond in each case to one line of Table A.

Table 133: Compounds 133.1–133.920

Compounds of the formula Ib in which $R^1$ is methyl and $R^2$ is trifluoromethyl, $R^5$ is methyl and $R^6$ is ethylcarbonyl and where for each individual compound the substituents $X^1$ and Het correspond in each case to one line of Table A.

Table 134: Compounds 134.1–134.920

Compounds of the formula Ib in which $R^1$ is methyl and $R^2$ is trifluoromethyl, $R^5$ is ethyl and $R^6$ is ethylcarbonyl and where for each individual compound the substituents $X^1$ and Het correspond in each case to one line of Table A.

Table 135: Compounds 135.1–135.920

Compounds of the formula Ib in which $R^1$ is methyl and $R^2$ is trifluoromethyl, $R^5$ is n-propyl and $R^6$ is ethylcarbonyl and where for each individual compound the substituents $X^1$ and Het correspond in each case to one line of Table A.

Table 136: Compounds 136.1–136.920

Compounds of the formula Ib in which $R^1$ is methyl and $R^2$ is trifluoromethyl, $R^5$ is methyl and $R^6$ is methylsulfonyl and where for each individual compound the substituents $X^1$ and Het correspond in each case to one line of Table A.

Table 137: Compounds 137.1–137.920

Compounds of the formula Ib in which $R^1$ is methyl and $R^2$ is trifluoromethyl, $R^5$ is ethyl and $R^6$ is methylsulfonyl and where for each individual compound the substituents $X^1$ and Het correspond in each case to one line of Table A.

Table 138: Compounds 138.1–138.920

Compounds of the formula Ib in which $R^1$ is methyl and $R^2$ is trifluoromethyl, $R^5$ is n-propyl and $R^6$ is methylsulfonyl and where for each individual compound the substituents $X^1$ and Het correspond in each case to one line of Table A.

Table 139: Compounds 139.1–139.920

Compounds of the formula Ib in which $R^1$ is methyl and $R^2$ is trifluoromethyl, $R^5$ is methyl and $R^6$ is ethylsulfonyl and where for each individual compound the substituents $X^1$ and Het correspond in each case to one line of Table A.

Table 140: Compounds 140.1–140.920

Compounds of the formula Ib in which $R^1$ is methyl and $R^2$ is trifluoromethyl, $R^5$ is ethyl and $R^6$ is ethylsulfonyl and where for each individual compound the substituents $X^1$ and Het correspond in each case to one line of Table A.

Table 141: Compounds 141.1–141.920

Compounds of the formula Ib in which $R^1$ is methyl and $R^2$ is trifluoromethyl, $R^5$ is n-propyl and $R^6$ is ethylsulfonyl and where for each individual compound the substituents $X^1$ and Het correspond in each case to one line of Table A.

Table 142: Compounds 142.1–142.920

Compounds of the formula Ib in which $R^1$ is methyl and $R^2$ is trifluoromethyl, $R^5$ is methyl and $R^6$ is 4-methylphenylsulfonyl and where for each individual compound the substituents $X^1$ and Het correspond in each case to one line of Table A.

Table 143: Compounds 143.1–143.920

Compounds of the formula Ib in which $R^1$ is methyl and $R^2$ is trifluoromethyl, $R^5$ is ethyl and $R^6$ is 4-methylphenylsulfonyl and where for each individual compound the substituents $X^1$ and Het correspond in each case to one line of Table A.

Table 144: Compounds 144.1–144.920

Compounds of the formula Ib in which $R^1$ is methyl and $R^2$ is trifluoromethyl, $R^5$ is n-propyl and $R^6$ is 4-methylphenylsulfonyl and where for each individual compound the substituents $X^1$ and Het correspond in each case to one line of Table A.

The compounds I and their agriculturally useful salts are suitable, both in the form of isomer mixtures and in the form of the pure isomers, as herbicides. The herbicidal compositions comprising I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the respective application method, the compounds I, or compositions comprising them, can additionally be employed in a further number of crop plants for eliminating undesirable plants. Examples of suitable crops are the following:

Allium cepa, Ananas comosus, Arachis hypogaea, Asparagus officinalis, Beta vulgaris spec. altissima, Beta vulgaris spec. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spec., Manihot esculenta, Medicago sativa, Musa spec., Nicotiana tabacum (N.rustica), Olea europaea, Oryza sativa, Phaseolus lunatus, Phaseolus vulgaris, Picea abies, Pinus spec., Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera and Zea mays.

In addition, the compounds I may also be used in crops which tolerate the action of herbicides owing to breeding, including genetic engineering methods.

The herbicidal compositions or the active compounds can be applied pre- or post-emergence. If the active compounds are less well tolerated by certain crop plants, application techniques may be used in which the herbicidal compositions are sprayed, with the aid of the spraying equipment, in such a way that they come into as little contact as possible, if any, with the leaves of the sensitive crop plants, while the active compounds reach the leaves of undesirable plants growing underneath, or the bare soil surface (post-directed, lay-by).

The compounds I, or the compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for scattering, or granules, by means of spraying, atomizing, dusting, scattering or watering. The use forms depend on the intended aims; in any case, they should ensure a very fine distribution of the active compounds according to the invention.

Essentiall suitable inert auxiliaries include: mineral oil fractions of medium to high boiling point, such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes or their derivatives, alcohols such as methanol, ethanol, propanol, butanol and cyclohexanol, ketones such as cyclohexanone, strongly polar solvents, e.g. amines such as N-methylpyrrolidone or water.

Aqueous use forms can be prepared from emulsion concentrates, suspensions, pastes, wettable powders or water-dispersible granules by adding water. To prepare emulsions, pastes or oil dispersions, the substituted 4-benzoylpyrazoles, either as such or dissolved in an oil or solvent, can be homogenized in water by means of a wetting agent, tackifier, dispersant or emulsifier. Alternatively, it is possible to prepare concentrates comprising active compound, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for scattering and dusts can be prepared by mixing or grinding the active compounds together with a solid carrier.

Granules, e.g. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate and ammonium nitrate, ureas, and products of vegetable origin, such as cereal meal, tree bark meal, wood meal and nutshell meal, cellulose powders, or other solid carriers.

The concentrations of the active compounds I in the ready-to-use preparations can be varied within wide ranges. In general, the formulations comprise from 0.001 to 98% by weight, preferably 0.01 to 95% by weight of at least one active compound. The active compounds are employed in a purity of from 90% to 100%, preferably 95% to 100% (according to the NMR spectrum).

The compounds I according to the invention can be formulated for example as follows:

I 20 parts by weight of the compound No. 26.39 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II 20 parts by weight of the compound No. 26.39 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III 20 parts by weight of the active compound No. 26.39 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV 20 parts by weight of the active compound No. 26.39 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V 3 parts by weight of the active compound No. 26.39 are mixed with 97 parts by weight of finely divided kaolin. This gives a dust which comprises 3% by weight of active compound.

VI 20 parts by weight of the active compound No. 26.39 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII 1 part by weight of the compound No. 26.39 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII 1 part by weight of the compound No. 26.39 is dissolved in a mixture composed of 80 parts by weight of cyclohexane and 20 parts by weight of Wettol® EM 31 (=nonionic emulsifier based on ethoxylated castor oil). This gives a stable emulsion concentrate.

To widen the spectrum of action and to achieve synergistic effects, the substituted 4-benzoylpyrazoles may be mixed with a large number of representatives of other herbicidal or growth-regulating active compound groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acid and its derivatives, benzoic acid and its derivatives, benzothiadiazinones, 2-aroyl-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- or hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or else concomitantly in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Nonphytotoxic oils and oil concentrates may also be added.

The rates of application of active compound are from 0.001 to 3.0, preferably 0.01 to 1.0, kg/ha of active substance (a.s.), depending on the control target, the season, the target plants and the growth stage.

The syntheses of some starting materials and products are described below.

2,4-Dichloro-3-((2-pyridyl)(hydroxymethyl)phenyl) (1-ethyl-5-hydroxy-1H-pyrazol-4-yl)methanone Step a: tert-Butyl 2,4-dichloro-3-((2-pyridyl) (hydroxymethyl))benzoate At −20° C., 4.0 g (39.6 mmol) of diisopropylamine in 120 ml of tetrahydrofuran are stirred for 40 minutes with 25.0 ml (40.0 mmol) of a 1.6 M n-butyllithium solution in hexane. At −75° C., a solution of 10.0 g (40.5 mmol) of tert-butyl 2,4-dichlorobenzoate in 30 ml of tetrahydrofuran is added dropwise, and the mixture is stirred for 1.5 h. A solution of 4.3 g (40.5 mmol) of 2-formylpyridine in 20 ml of tetrahydropyran is added dropwise and the mixture is stirred at room temperature for 2.5 h. The mixture is poured into 500 ml of saturated aqueous ammonium chloride solution and extracted with ethyl acetate. The combined extracts are washed with water, dried over sodium sulfate, filtered and freed from the solvent under reduced pressure. The crude product is purified by silica gel chromatography using cyclohexane/ethyl acetate. Yield: 7.5 g; $^1$H NMR, δ [ppm], (DMSO-$d_6$): 1.5 (s), 6.5 (m), 7.2 (m); 7.5 (m), 7.9 (m), 8.4 (d)

Step b: 2,4-Dichloro-3-((2-pyridyl)(hydroxymethyl)) benzoic acid 3.5 g (9.9 mmol) of tert-butyl 2,4-dichloro-3-((2-pyridyl) (hydroxymethyl))benzoate in 120 ml of toluene and 60 ml of water together with 1.9 g of p-toluenesulfonic acid are heated under reflux for 9 h. After cooling, the organic phase is separated off and the aqueous phase is admixed with a solution of 23.8 g of sodium dihydrogen phosphate in 280 ml of water and extracted with ethyl acetate. The combined organic phases are dried over sodium sulfate, filtered and freed from the solvent under reduced pressure. Yield: 1.9 g; $^1$H NMR, δ [ppm], (DMSO-$d_6$): 6.5 (m), 7.2 (m), 7.5 (d), 7.6 (d), 7.95 (m), 8.4 (d), 13.5 (broad s)

Step c: (2,4-Dichloro-3-((2-pyridyl)(hydroxymethyl) phenyl)(1-ethyl-5-hydroxy-1H-pyrazol-4-yl)methanone (Table 2, Example 319; Comp. No. 2.319)

At room temperature, 1.7 g (5.7 mmol) of 2,4-dichloro-3-((2-pyridyl)(hydroxymethyl))benzoic acid, 0.6 g (5.7 mmol) of 1-ethyl-5-hydroxy-1H-pyrazole and 1.2 g (5.7 mmol) of N,N-dicyclohexylcarbodiimide in 25 ml of acetonitrile are stirred for 3 d. The reaction mixture is taken up in 50 ml of 2% strength aqueous sodium hydrogen carbonate solution, filtered and extracted with ethyl acetate. The combined organic phases are dried over sodium sulfate, filtered and freed from the solvent under reduced pressure. The intermediate is dissolved in 10 ml of 1,4-dioxane, admixed with 1.0 g (7.1 mmol) of potassium carbonate and heated under reflux for 8 h. After cooling, the reaction mixture is taken up in 80 ml of water and extracted with methyl tert-butyl ether. The product is precipitated from the aqueous phase by acidification with dilute aqueous hydrochloric acid. $^1$H NMR, δ [ppm], (DMSO-$d_6$): 1.3 (t), 4.0 (q), 6.6 (s), 7.2 (s), 7.3 (m), 7.4 (d), 7.5 (d), 7.8 (d), 7.9 (m), 8.0 (d)

2,4-Dichloro-3-((2-furyl)(hydroxymethyl)phenyl)(1-ethyl-5-hydroxy-1H-pyrazol-4-yl)methanone This compound was prepared similarly to the abovementioned procedures. $^1$H NMR, δ [ppm], (DMSO-$d_6$): 1.3 (t), 3.9 (q), 6.3 (m), 6.4 (broad s); 6.4 (m), 6.5 (m), 7.3 (s), 7.4 (d), 7.6 (m)

Step a: tert-Butyl 2,4-dichloro-3-((2-furyl)(hydroxymethyl)) benzoate

At −20° C., 4.0 g (39.6 mmol) of diisopropylamine in 80 ml of tetrahydrofuran are treated for 15 min with 19 ml (30.4 mmol) of 1.6 M n-butyllithium solution in hexane. After cooling to −75° C., a solution of 7.5 g (30.4 mmol) of tert-butyl 2,4-dichlorobenzoate in 20 ml of tetrahydrofuran is added dropwise and the mixture is stirred at room temperature for 12 h. The reaction mixture is admixed with a solution of 2.9 g (30.2 mmol) of 2-formylfuran in 15 ml of tetrahydrofuran and stirred at room temperature for a further 12 h. The mixture is taken up in 300 ml of saturated aqueous sodium chloride solution and extracted with ethyl acetate. The combined organic phases are dried over sodium sulfate, filtered and freed from the solvent under reduced pressure. Yield: 9.2 g; $^1$H-NMR, δ [ppm], (CDCl$_3$): 1.6 (s), 3.6 (d), 6.2 (m), 6.3 (m), 7.4 (m), 7.7 (d), 7.4 (m), 7.5 (d)

Step b: tert-Butyl 2,4-dichloro-3-((2-furyl) (methoxymethyl))benzoate

At room temperature, 3.0 g (8.8 mmol) of tert-butyl 2,4-dichloro-3-((2-furyl)(hydroxymethyl))benzoate in 40 ml of tetrahydrofuran are stirred for 1 h with 0.4 g (16.6 mmol) of sodium hydride. 6.3 g (43.8 mmol) of iodomethane are added dropwise and the mixture is stirred at room temperature for a further 3 h. The reaction mixture is taken up in 100 ml of saturated aqueous sodium chloride solution, extracted with methyl tert-butyl ether, dried over sodium sulfate, filtered and freed from the solvent under reduced pressure. The crude product is purified by silica gel chromatography using cyclohexane/ethyl acetate. Yield: 2.7 g; $^1$H NMR, δ [ppm], (CDCl$_3$): 1.6 (s), 3.5 (s), 6.2 (m), 6.3 (m), 7.4 (m), 7.5 (d)

Step c: 2,4-Dichloro-3-((2-furyl)(methoxymethyl))benzoic acid 2.3 g (6.4 mmol) of tert-butyl 2,4-dichloro-3-((2-furyl) (methoxymethyl))benzoate in 50 ml of methanol and 15 ml of water are heated under reflux with 0.7 g (16.1 mmol) of sodium hydroxide for 4 h. 5.0 ml of a 10% strength aqueous sodium hydroxide solution are added and the mixture is heated for a further 3 h. After the reaction mixture has been concentrated under reduced pressure, 50 ml of water are added and the reaction mixture is extracted with dichloromethane. The aqueous phase is acidified using 10% strength aqueous hydrochloric acid and the product is extracted with ethyl acetate. The combined organic phases are dried over sodium sulfate, filtered and freed from the solvent under reduced pressure. Yield 1.8 g.

Step d: (2,4-Dichloro-3-((2-furyl)(methoxymethyl)phenyl) (1-ethyl-5-hydroxy-1H-pyrazol-4-yl)methanone (Table 2, Example 362; Comp. No. 2.362)

1.4 g (4.7 mmol) of 2,4-dichloro-3-((2-furyl) (methoxymethyl))benzoic acid, 0.5 g (4.7 mmol) of 1-ethyl-5-hydroxy-1H-pyrazole and 1.0 g (4.7 mmol) of N,N-dicyclohexylcarbodiimide in 10 ml of acetonitrile are stirred at room temperature for 24 h. The reaction mixture is stirred into a 2% strength aqueous sodium hydrogen carbonate solution, extracted with ethyl acetate, dried over sodium sulfate, filtered and freed from the solvent under reduced pressure. The intermediate is purified by silica gel chromatography using ethyl acetate/cyclohexane (Yield: 0.5 g), dissolved in 3 ml of 1,4-dioxane, admixed with 0.2 g (1.2 mmol) of potassium carbonate and heated under reflux for 4 h. The reaction mixture is concentrated under reduced pressure, taken up in 40 ml of water and extracted with methylene chloride. The product is precipitated by acidification of the aqueous phase using 10% strength aqueous hydrochloric acid. Yield: 190 mg; mp. 92 to 93° C.

(2,4-Dichloro-3-((3-furyl)(hydroxymethyl)phenyl) (1-ethyl-5-hydroxy-1H-pyrazol-4-yl)methanone (Table 2, Example 250; Comp. No. 2.250)

This compound is prepared similarly to the abovementioned procedures. $^1$H NMR, δ [ppm], (DMSO-d$_6$): 1.3 (t), 3.9 (q), 6.1 (broad s), 6.4 (s), 6.5 (s), 7.3 (broad s.), 7.4 (d), 7.5 (s), 7.5 (d), 7.6 (s)

(2,4-Dichloro-3-((3-furyl)(methoxymethyl)phenyl) (1-ethyl-5-hydroxy-1H-pyrazol-4-yl)methanone (Table 2, Example 365; Comp. No. 2.365)

This compound is prepared similarly to the abovementioned procedures. $^1$H NMR, δ [ppm], (DMSO-d$_6$): 1.3 (t), 3.3 (s), 3.9 (q), 6.1 (s), 6.4 (s), 7.3 (broad s), 7.4 (d), 7.5 (s), 7.6 (d), 7.6 (s)

2,4-Dichloro-3-(3-(5H-furanone)methyl)phenyl)-(1-ethyl-5-hydroxy-1H-pyrazol-4-yl)methanone Step a: 2,4-Dichloro-3-(3-(5H-furanone)methyl)benzoic acid The solution of 13 g (0.038 mol) of tert-butyl 2,4-dichloro-3-(3-furyl)hydroxymethylbenzoate (similar to Ex. 2.362 step a) and 1.8 g of p-toluenesulfonic acid in 370 ml of toluene are refluxed for 6 h. The mixture is subsequently poured into 100 ml of 10% strength aqueous sodium hydroxide solution and extracted with ethyl acetate. The aqueous phase is acidified using hydrochloric acid and extracted repeatedly with ethyl acetate. The combined organic phases are washed with water, dried and concentrated. This gives 4.8 g (45%) of the title compound, mp. 196° C.

Step b: 2,4-Dichloro-3-(3-(5H-furanone)methyl)phenyl)-(1-ethyl-5-hydroxy-1H-pyrazol-4-yl)methanone

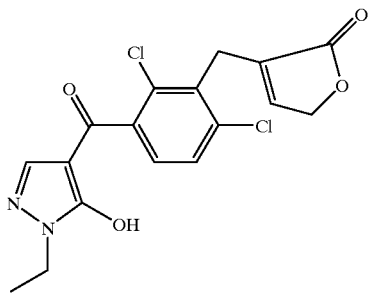

1.1 g (0.0035 mol) of 2,4-dichloro-3-(3-(5H-furanone) methyl)benzoic acid, 0.4 g (0.0035 mol) of 1-ethyl-5-hydroxy-1H-pyrazole and 0.72 g (0.0035 mol) of dicyclohexylcarbodiimide are stirred in 15 ml of acetonitrile at room temperature for 12 h. The reaction mixture is poured into 100 ml of 2% strength aqueous sodium bicarbonate solution and extracted with ethyl acetate. The organic phase is dried and concentrated.

1 g of the residue obtained in this manner and 0.5 g (0.0034 mol) of potassium carbonate in 5 ml of dioxane are refluxed for 5 h. After cooling, the mixture is diluted with 60 ml of water and extracted successively with methylene chloride and methyl tert-butyl ether. The aqueous phase is separated off and acidified with HCl, and the precipitate is filtered off with suction (23%; mp. 90–93° C.).

TABLE 145

| No. | R$^5$ | R$^6$ | Het | mp. [° C] | $^1$H NMR [ppm] |
|---|---|---|---|---|---|
| 145.1 | CH$_3$ | H | 5-methyl-4,5-di-hydro-3-isoxazolyl | 90 | |
| 145.2 | CH$_3$ | H | 5-chloromethyl-4,5-dihydro-3-isoxazolyl | 93 | |
| 145.3 | CH$_3$ | iso-propyl | 5-chloromethyl-4,5-dihydro-3-isoxazolyl | 72 | |
| 145.4 | CH$_3$ | SO$_2$CH$_3$ | 5-chloromethyl-4,5-dihydro-3-isoxazolyl | 87 | |
| 145.5 | C$_2$H$_5$ | H | 4,5-dihydro-3-isoxazolyl | 136 | |
| 145.6 | C$_2$H$_5$ | H | 5-methyl-4,5-dihydro-3-isoxazolyl | 92 | |
| 145.7 | C$_2$H$_5$ | iso-propyl | 5-methyl-4,5-dihydro-3-isoxazolyl | 66 | |

Use Examples

The herbicidal activity of the substituted 4-benzoylpyrazoles of the formula I was demonstrated by the following greenhouse experiments:

The culture containers used were plastic pots containing loamy sand with approximately 3.0% of humus as the substrate. The seeds of the test plants were sown separately for each species.

For the pre-emergence treatment, the active compounds, which had been suspended or emulsified in water, were applied directly after sowing by means of finely distributing nozzles. The containers were irrigated gently to promote germination and growth and subsequently covered with translucent plastic hoods until the plants had rooted. This cover causes uniform germination of the test plants, as long as this was not adversely affected by the active compounds.

For the post-emergence treatment, the test plants were first grown to a height of 3 to 15 cm, depending on the plant habit, and only then treated with the active compounds which had been suspended or emulsified in water. The test plants were for this purpose either sown directly and grown in the same containers, or they were first grown separately as seedlings and transplanted into the test containers a few days prior to treatment. The rate of application for the post-emergence treatment was 0.5 or 0.25 kg/ha of a.s.

Depending on the species, the plants were kept at 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial parts, and 0 means no damage, or normal course of growth.

The plants used in the greenhouse experiments belong to the following species:

| Scientific name | Common name |
| --- | --- |
| *Chenopodium album* | lambsquarters (goosefoot) |
| *Echinochloa crus-galli* | barnyardgrass |
| *Setaria faberii* | giant foxtail |
| *Setaria viridis* | green foxtail |
| *Zea mays* | corn |

Selective herbicidal activity when applied post-emergence in the greenhouse

Comp. No. 145.5

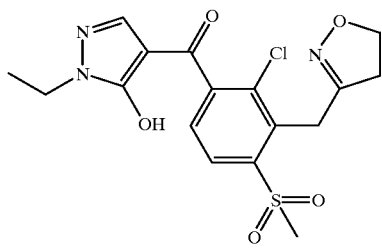

The compound No. 145.5, applied post-emergence, controlled the abovementioned weeds very efficiently at application rates of 0.5 or 0.25 kg/ha of a.s.

What is claimed is:

1. A 4-benzoylpyrazole of the formula I

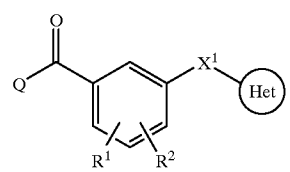

where:

$R^1$ and $R^2$ are each hydrogen, mercapto, nitro, halogen, cyano, thiocyanato, $C_1$–$C_6$-alkyl, $C_1$–$C_6$-haloalkyl, $C_1$–$C_6$-alkoxy, $C_2$–$C_6$-alkenyl, $C_2$–$C_6$-alkynyl, —$OR^3$, —$OCOR^3$, —$OSO_2R^3$, —$S(O)_nR^3$, —$SO_2OR^3$, —$SO_2N(R^3)_2$, —$NR^3SO_2R^3$ or —$NR^3COR^3$;

$R^3$ is hydrogen, $C_1$–$C_6$-alkyl, $C_1$–$C_6$-haloalkyl, $C_2$–$C_6$-alkenyl, $C_2$–$C_6$-alkynyl, phenyl or phenyl-$C_1$–$C_6$-alkyl; where the alkyl radicals mentioned may be partially or fully halogenated and/or carry one to three of the following groups:

hydroxyl, mercapto, amino, cyano, $R^3$, —$OR^3$, —$SR^3$, —$N(R^3)_2$, =$NOR^3$, —$OCOR^3$, —$SCOR^3$, —$NR^3COR^3$, —$CO_2R^3$, —$COSR^3$, —$CON(R^3)_2$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the eight last-mentioned radicals may in turn be substituted;

n is 0, 1 or 2;

Q is a pyrazole of the formula II which is attached in position 4,

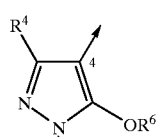

where $R^4$ is hydrogen, $C_1$–$C_6$-alkyl or $C_1$–$C_6$-haloalkyl;

$R^5$ is $C_1$–$C_6$-alkyl, $C_1$–$C_6$-haloalkyl, phenyl or phenyl which may be partially or fully halogenated and/or carry one to three of the following radicals:

nitro, cyano, $C_1$–$C_4$-alkyl, $C_1$–$C_4$-haloalkyl, $C_1$–$C_4$-alkoxy, $C_1$–$C_4$-haloalkoxy;

$R^6$ is hydrogen, $C_1$–$C_6$-alkyl, $C_1$–$C_6$-haloalkyl, $C_1$–$C_6$-alkylcarbonyl, $C_1$–$C_6$-haloalkylcarbonyl, $C_1$–$C_6$-alkoxycarbonyl, $C_1$–$C_6$-alkylsulfonyl, $C_1$–$C_6$-haloalkylsulfonyl, phenylcarbonyl, phenylcarbonylmethyl, phenoxycarbonyl or phenylsulfonyl, where the four last-mentioned substituents are either unsubstituted, or the phenyl ring may in each case be partially or fully halogenated and/or carry one to three of the following radicals:

nitro, cyano, $C_1$–$C_4$-alkyl, $C_1$–$C_4$-haloalkyl, $C_1$–$C_4$-alkoxy, $C_1$–$C_4$-haloalkoxy;

$X^1$ is a straight-chain or branched $C_1$–$C_6$-alkylene, a $C_2$–$C_6$-alkenylene or a $C_2$–$C_6$-alkynylene chain, where the alkylene, alkenylene or alkynylene radicals mentioned may be partially halogenated and/or carry one to three of the following groups:

—$OR^7$, —$OCOR^7$, —$OCONHR^7$ or —$OSO_2R^7$, and where those of the alkenylene radicals mentioned are excluded where the double bond is α,β to the phenyl ring and where Het is linked to the double bond via the β position;

$R^7$ is hydrogen, $C_1$–$C_6$-alkyl, $C_2$–$C_6$-alkenyl, $C_2$–$C_6$-alkynyl, phenyl, phenyl-$C_1$–$C_6$-alkyl, where the alkyl, alkenyl or alkynyl radicals mentioned may be partially or fully halogenated and/or substituted by one or more of the following radicals:

hydroxyl, mercapto, amino, cyano, nitro, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy;

Het is a three- to six-membered, partially or fully saturated heterocyclic group or a three- to six-membered heteroaromatic group having up to three hetero atoms selected from the group consisting of:

nitrogen, oxygen and sulfur, where the heterocyclic or heteroaromatic group mentioned may be partially or fully halogenated and/or substituted by $R^8$;

and when Het is a piperidinyl radical it is 2-piperidinyl, 3-piperidinyl or 4-piperidinyl;

$R^8$ is hydrogen, hydroxyl, mercapto, amino, cyano, nitro, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy, where in all instances each of the alkyl radicals may be substituted by one or more of the following radicals:

cyano, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy;

and agriculturally useful salts thereof.

2. A 4-benzoylpyrazole of the formula I as claimed in claim 1, in which $R^1$ is nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^3$ or —$S(O)_nR^3$;

$R^2$ is hydrogen or one of the radicals mentioned above under $R^1$.

3. A 4-benzoylpyrazole of the formula Ia as claimed in claim 1,

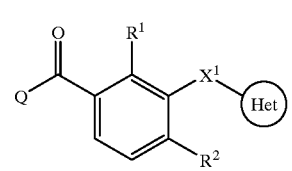

Ia where the substituents $R^1$, $R^2$, Q, $X^1$ and Het are each as defined under claim 1.

4. A 4-benzoylpyrazole of the formula Ia as claimed in claim 3 in which $X^1$ is a $C_1$–$C_2$-alkylene or $C_2$-alkynylene chain.

5. A 4-benzoylpyrazole of the formula Ia as claimed in claim 1 in which Het is a five- or six-membered, partially or fully saturated heterocyclic or a five- or six-membered heteroaromatic group having up to three hetero atoms selected from the group consisting of nitrogen, oxygen and sulfur.

6. A process for preparing 4-benzoylpyrazoles of the formula I as claimed in claim 1, which comprises acylating a pyrazole of the formula Ia in which the substituents $R^5$ and $R^4$ are each as defined under claim 1

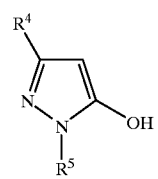

IIa with an activated carboxylic acid IIIa or with a carboxylic acid IIIb,

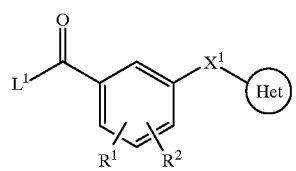

IIIa

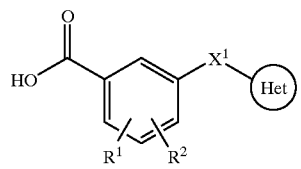

IIIb where the substituents $R^1$, $R^2$, $X^1$ and Het are each as defined in claim 1 and $L^1$ is a nucleophilically replaceable leaving group, and rearranging the acylation product, if appropriate in the presence of a catalyst, to the compounds I and, if desired, reacting it with a compound of the formula IV, $$L^2\text{—}R^6 \qquad \text{IV}$$

(where $R^6 \neq H$)

in which $R^6$ is as defined in claim 1, except for hydrogen, and $L^2$ is a nucleophilically replaceable leaving group, for preparing 4-benzoylpyrazoles of the formula I where $R^6 \neq H$.

7. A composition comprising a herbicidally effective amount of at least one 4-benzoylpyrazole of the formula I or an agriculturally useful salt of I as claimed in claim 1 and auxiliaries customary for the formulation of crop protection agents.

8. A process for preparing herbicidally effective compositions as claimed in claim 7, which comprises mixing a herbicidally effective amount of at least one 4-benzoylpyrazole of the formula I or an agriculturally useful salt of I and auxiliaries customary for the formulation of crop protection agents.

9. A process for controlling undesirable vegetation, which comprises allowing a herbicidally effective amount of at least one 4-benzoylpyrazole of the formula I or an agriculturally useful salt of I as claimed in claim 1 to act on plants, their habitat and/or on seeds.

* * * * *

UNITED STATES PATENT AND TRADEMARK OFFICE
CERTIFICATE OF CORRECTION

PATENT NO. : 6,156,702
DATED : December 5, 2000
INVENTOR(S) : Engel et al.

It is certified that error appears in the above-identified patent and that said Letters Patent is hereby corrected as shown below:

<u>Column 54, claim 6,</u>
Line 9, "formula Ia" should be -- formula IIa --.

Signed and Sealed this

Second Day of October, 2001

*Attest:*

*Nicholas P. Godici*

NICHOLAS P. GODICI
*Attesting Officer*    *Acting Director of the United States Patent and Trademark Office*